United States Patent
Jonas et al.

(10) Patent No.: US 7,569,605 B2
(45) Date of Patent: Aug. 4, 2009

(54) METHODS OF TREATING CENTRAL NERVOUS SYSTEM DISORDERS WITH A LOW DOSE COMBINATION OF ESCITALOPRAM AND BUPROPION

(75) Inventors: Jeffrey Jonas, Hoboken, NJ (US); Anjana Bose, Roseland, NJ (US); Joyce Tsai, New York, NY (US)

(73) Assignee: Forest Laboratories Holdings Limited (BM)

( * ) Notice: Subject to any disclaimer, the term of this patent is extended or adjusted under 35 U.S.C. 154(b) by 169 days.

(21) Appl. No.: 11/549,714

(22) Filed: Oct. 16, 2006

(65) Prior Publication Data

US 2007/0203231 A1 Aug. 30, 2007

Related U.S. Application Data

(60) Provisional application No. 60/727,276, filed on Oct. 14, 2005, provisional application No. 60/810,882, filed on Jun. 2, 2006, provisional application No. 60/804,086, filed on Jun. 6, 2006.

(51) Int. Cl.
*A61K 31/34* (2006.01)
*A61K 31/195* (2006.01)

(52) U.S. Cl. .................................. 514/469; 514/563
(58) Field of Classification Search ................. 514/469, 514/563

See application file for complete search history.

(56) References Cited

U.S. PATENT DOCUMENTS

| | | | |
|---|---|---|---|
| 3,819,706 A | 6/1974 | Mehta et al. | |
| 3,885,046 A | 5/1975 | Mehta | |
| 4,723,958 A | 2/1988 | Pope et al. | |
| 5,007,790 A | 4/1991 | Shell | |
| RE33,994 E | 7/1992 | Baker et al. | |
| RE34,712 E | 8/1994 | Boegesoe et al. | |
| 5,358,970 A | 10/1994 | Ruff et al. | |
| 5,427,798 A | 6/1995 | Ludwig et al. | |
| 5,472,708 A | 12/1995 | Chen | |
| 5,508,040 A | 4/1996 | Chen | |
| 5,582,837 A | 12/1996 | Shell | |
| 5,656,294 A | 8/1997 | Friend et al. | |
| 5,731,000 A | 3/1998 | Ruff et al. | |
| 5,763,493 A | 6/1998 | Ruff et al. | |
| 5,840,329 A | 11/1998 | Bai | |
| 5,972,389 A | 10/1999 | Shell et al. | |
| 6,096,341 A | 8/2000 | Seth | |
| 6,143,327 A | 11/2000 | Seth | |
| 6,217,904 B1 | 4/2001 | Midha et al. | |
| 6,342,496 B1 | 1/2002 | Jerussi et al. | |
| 6,372,254 B1 | 4/2002 | Ting et al. | |
| 6,500,457 B1 | 12/2002 | Midha et al. | |
| 6,555,136 B2 | 4/2003 | Midha et al. | |
| 6,566,540 B2 | 5/2003 | Rock et al. | |
| 6,627,223 B2 | 9/2003 | Percel et al. | |
| 6,730,321 B2 | 5/2004 | Ting et al. | |
| 6,793,936 B2 | 9/2004 | Devane et al. | |
| 6,905,708 B2 | 6/2005 | Li et al. | |
| 2002/0052340 A1 | 5/2002 | Jerussi et al. | |
| 2003/0124196 A1 | 7/2003 | Weinbach et al. | |
| 2003/0133978 A1 | 7/2003 | Davis et al. | |
| 2003/0161874 A1 | 8/2003 | Li et al. | |
| 2004/0028729 A1 | 2/2004 | Shojaei et al. | |
| 2004/0167209 A1 | 8/2004 | Dancer et al. | |
| 2004/0198809 A1 | 10/2004 | Sanchez et al. | |
| 2005/0147678 A1 | 7/2005 | Li et al. | |
| 2005/0196453 A1 | 9/2005 | Jensen et al. | |
| 2005/0197388 A1 | 9/2005 | Jensen et al. | |
| 2006/0058293 A1 * | 3/2006 | Weber et al. | ............. 514/232.5 |

FOREIGN PATENT DOCUMENTS

| | | |
|---|---|---|
| WO | WO-96/26718 | 9/1996 |
| WO | WO-98/55107 | 12/1998 |
| WO | WO99/38504 A1 * | 8/1999 |
| WO | WO-01/03694 | 1/2001 |
| WO | WO-01/22941 | 4/2001 |
| WO | WO02/10169 A * | 2/2002 |
| WO | WO-02/087566 | 11/2002 |
| WO | WO-03/000672 | 1/2003 |
| WO | WO-03/006449 | 1/2003 |
| WO | WO-03/011278 | 2/2003 |
| WO | WO-03/051861 | 6/2003 |
| WO | WO-2004/058299 | 7/2004 |
| WO | WO-2004/083197 | 9/2004 |

OTHER PUBLICATIONS

Symposia: Escitalopram has potential in anxiety disorder. Inpharma Apr. 26, 2002, ISSN: 1173-8324.*

DeVane, *J. Clin. Psychiatry* 2003, 64 (suppl. 18):14-19.

Gerner et al., *Biol. Psychiatry*, 1998, 43:101S, abstract 336.

(Continued)

*Primary Examiner*—Jennifer Myong M Kim
(74) *Attorney, Agent, or Firm*—Michael Ciraolo

(57) ABSTRACT

The present invention relates to a method of treating a central nervous system disorder, such as a mood disorder (e.g., major depressive disorder) or an anxiety disorder (e.g., general anxiety disorder, social anxiety disorder, post traumatic stress disorder, and panic disorder) with a low dose combination of escitalopram and bupropion.

9 Claims, 3 Drawing Sheets

OTHER PUBLICATIONS

Kennedy et al. *J. Clin. Psychiatry,* 2002, 63: 181-186.
Gerner et al, *Biol. Psychiatry,* 1998, 43:99S, abstract 329.
Ashton et al., *J. Clin. Psychiatry,* 1998, 59(3):112-115.
Gitlin et al., *J. Sex & Marital Therapy* 2002, 28:131-138.
Sturpe et al., *J. Family Practice* Aug. 2002, 51(8):1681.
Fava et al., Psychiatr. Clin. North Am., 1996, 19(2):179-200.
Fava et al., Ann. Clin. Psychiatry, 2003, 15(1): 17-22.
Lam et al., J. Clin. Psychiatry, 2004, 65:337-340.
Trindade et al., Adverse Effects Associated with Selective Serotonin Reuptake Inhibitors and Tricyclic Antidepressants: A Meta-analysis, Canadian Medical Association Journal. Nov. 1998, 159 (10): 1245-1252.
Phillips et al., Depression and Sexual Desire, American Family Physician [online], Aug. 15, 2000, vol. 62, No. 4, retrieved from the internet:<URL: http://www.aafgp.org/afp/20000815/782.html>.
Rampello et al., Dopamine and Depression: Therapeutic Implications CNS Drugs, Jan. 2000, 13(1): 35-45.
International Search Report for PCT/US06/60006, mailed Sep. 25, 2007.
Written Opinion of the International Search Authority for PCT/US06/60006, mailed Sep. 25, 2007.

* cited by examiner

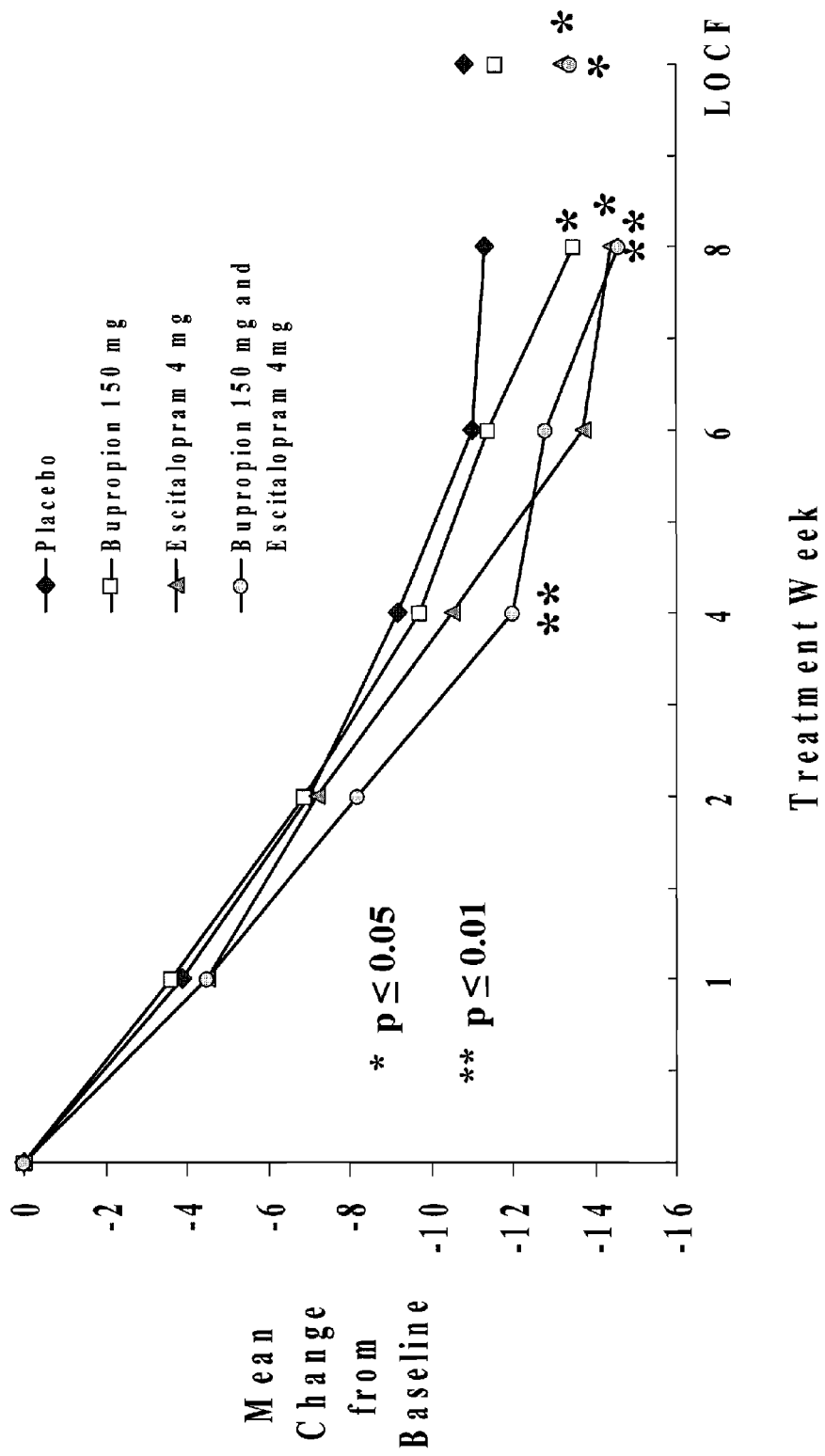
Figure 1: MADRS Results

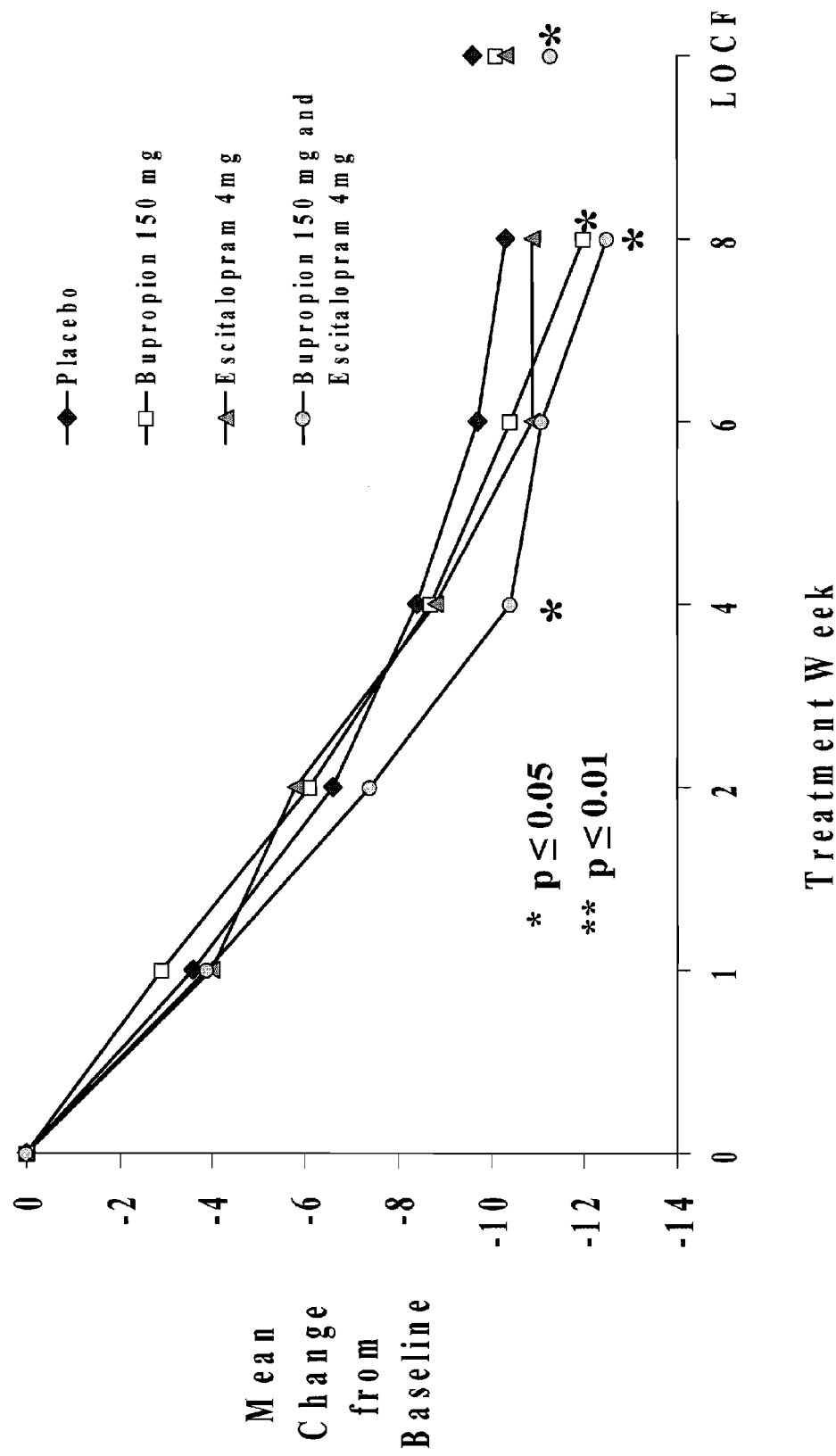
Figure 2: HAMD$_{24}$ Results

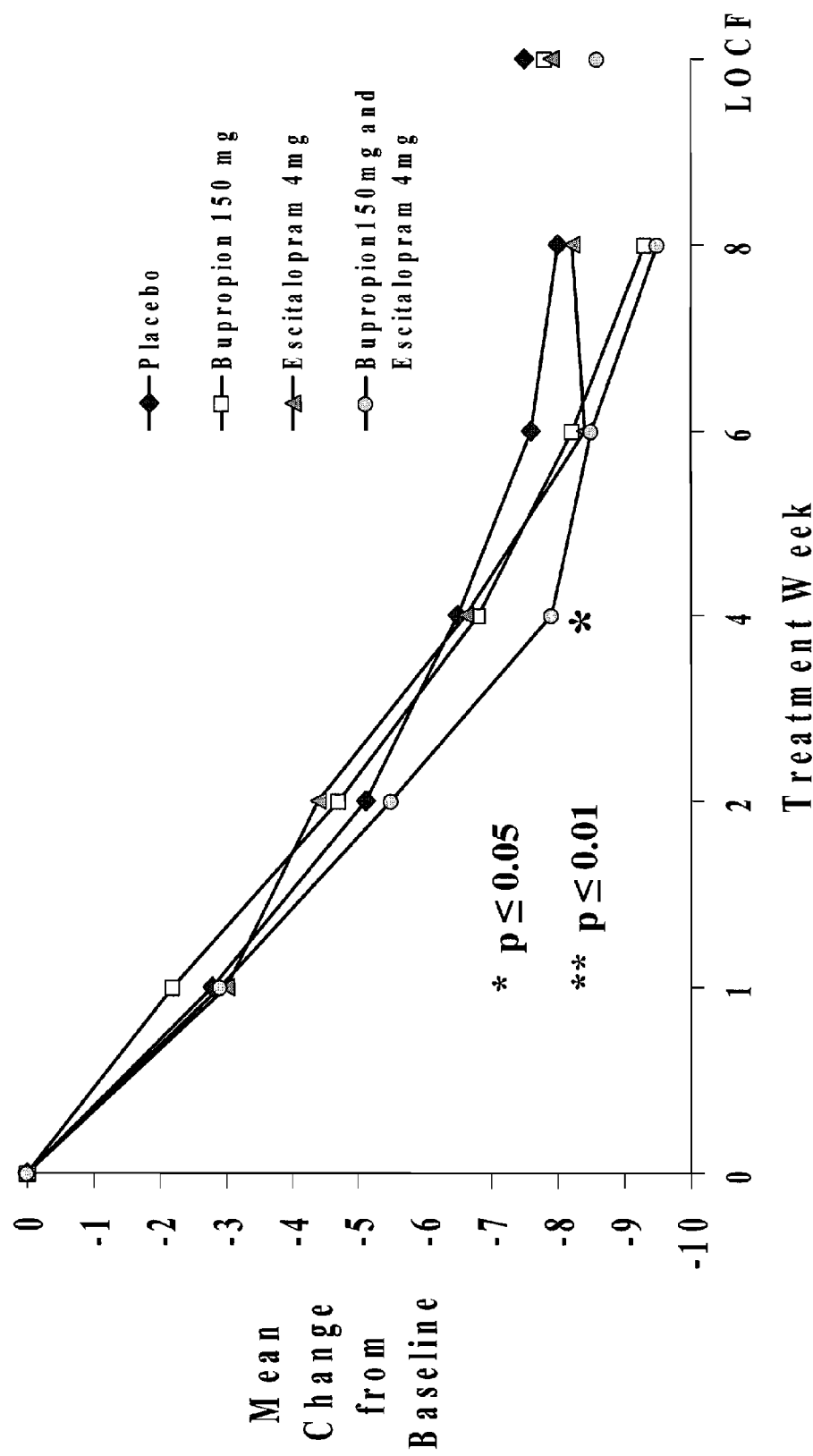

METHODS OF TREATING CENTRAL NERVOUS SYSTEM DISORDERS WITH A LOW DOSE COMBINATION OF ESCITALOPRAM AND BUPROPION

This application claims priority to U.S. Provisional Application No. 60/727,276 filed Oct. 14, 2005, U.S. Provisional Application No. 60/810,882 filed Jun. 2, 2006, and U.S. Provisional Application No. 60/804,086 filed Jun. 6, 2006, the disclosures of all of which are hereby incorporated by reference in their entireties.

FIELD OF THE INVENTION

The present invention relates a method of treating a central nervous system disorder, such as a mood disorder (e.g., major depressive disorder) or an anxiety disorder (e.g., general anxiety disorder, social anxiety disorder, post traumatic stress disorder, or panic disorder) with a low dose combination of escitalopram and bupropion.

BACKGROUND OF THE INVENTION

Selective serotonin reuptake inhibitors (hereinafter called SSRIs), such as racemic citalopram and escitalopram, have become first-choice therapeutics in the treatment of depression primarily due to their superior efficacy compared to tricyclic antidepressants and monoamine oxidase inhibitors (MAOIs). SSRIs function by inhibiting the reuptake of the neurotransmitter serotonin (5-hydroxytryptamine, 5-HT) by nerve cells at synapses. As a result, serotonin persists in the synaptic gap and has the chance to stimulate receptors of recipient cells.

There is typically a delay (e.g., 2 weeks) between the initiation of SSRI treatment and an observed therapeutic affect. The neurological bases for the delay is that administration of SSRIs immediately increases synaptic serotonin and stimulates the inhibitory $5\text{-HT}_{1A}$ autoreceptor, turning down spontaneous firing of 5-HT neurons. After continued SSRI administration, the $5\text{-HT}_{1A}$ autoreceptor desensitizes and normal firing of the 5-HT neuron returns.

Escitalopram is the S-enantiomer of citalopram and has the following structure:

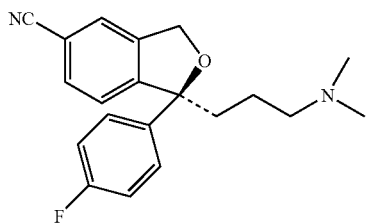

Methods of preparing escitalopram are disclosed in, for example, U.S. Pat. Nos. Re. 34,712 and 6,566,540 and International Publication Nos. WO 03/000672, WO 03/006449, WO 03/051861, and WO 2004/083197, all of which are hereby incorporated by reference.

International Publication Nos. WO 01/03694 and WO 02/087566, which are hereby incorporated by reference, disclose the use of escitalopram in the treatment of various mental disorders including major depressive disorder, general anxiety disorder, social anxiety disorder, post traumatic stress disorder, panic attacks, acute stress disorder, eating disorders (such as bulimia, anorexia and obesity), phobias, dysthymia, premenstrual syndrome, cognitive disorders, impulse control disorders, attention deficit hyperactivity disorder and drug abuse. International Publication No. WO 02/087566 also discloses the use of escitalopram for the treatment of patients who have failed to respond to initial treatment with a conventional SSRI, in particular patients with major depression disorder who have failed to respond to initial treatment with a conventional SSRI.

Escitalopram oxalate is currently marketed in the United States as Lexapro® for the treatment of major depressive disorder and generalized anxiety disorder. Lexapro® is available in 5, 10 and 20 mg escitalopram immediate release tablets (as an oxalate salt) and in a 5 mg/mL oral solution.

A modified release formulation of escitalopram oxalate prepared by melt granulation is disclosed in International Publication No. WO 01/22941. Modified release formulations of SSRIs, such as citalopram hydrobromide and escitalopram oxalate, having particular dissolution profiles are disclosed in International Publication No. WO 2004/058299.

Side effects associated with esitalopram include nausea, insomnia, somnolence, increased sweating, fatigue, and sexual dysfunction (including, but not limited to, ejaculation disorder, anorgasmia, and decreased libido).

Bupropion hydrochloride, which is described in U.S. Pat. Nos. 3,819,706 and 3,885,046, is currently marketed as Wellbutrin®, Wellbutrin SR®, and Wellbutrin XL® for the treatment of major depressive disorder and Zyban® as an aid to smoking cessation treatment. Bupropion is an aminoketone-derivative chemically unrelated to other currently available antidepressants (e.g., selective serotonin-reuptake inhibitors, tricyclics, and tetracyclics). While the neurochemical mechanisms of the antidepressant and smoking cessation effects are unknown, noradrenergic pathways and/or dopaminergic effects appear to be primarily involved. Bupropion does not inhibit monoamine oxidase and is a weak blocker of serotonin and norepinephrine uptake.

Wellbutrin® (an immediate release bupropion hydrochloride formulation) is supplied as 75 and 100 mg tablets which are to be administered three times a day, preferably with at least 6 hours between successive doses. Controlled release formulations of bupropion hydrochloride have been developed.

For example, U.S. Pat. No. Re. 33,994 discloses a controlled release bupropion tablet formulation comprising a bupropion hydrochloride core and a coating comprised of a water-insoluble, water-permeable film forming coating and a particulate, water-soluble, pore-forming material. However, because 25-70% of the bupropion is released within 4 hours and 40-90% within 6 hours, at least twice daily dosing is still typically required.

U.S. Pat. Nos. 5,358,970, 5,763,493, and 5,731,000 disclose bupropion hydrochloride formulations containing a stabilizer to prevent the degradation of the bupropion hydrochloride.

U.S. Pat. No. 5,427,798 discloses a controlled release bupropion tablet formulation containing hydroxypropyl methylcellulose. More than half of the bupropion is preferably released in distilled water in 4 hours. Because of this rapid release rate, the formulation typically is administered multiple times in a day.

U.S. Pat. Nos. 6,096,341 and 6,143,327 disclose a controlled release tablet of bupropion hydrochloride, free of stabilizers and pore-forming agents. The tablet is comprised of a core consisting essentially of bupropion hydrochloride, a binder, and a lubricant, and a coating consisting essentially of a water-insoluble, water-permeable, film-forming polymer, a plasticizer, and a water-soluble polymer.

U.S. Pat. No. 6,905,708 and U.S. Patent Application Publication Nos. 2003/0161874 and 2005/0147678 disclose a once a day bupropion hydrochloride formulation comprising coated pellets of bupropion hydrochloride.

In DeVane, *J. Clin. Psychiatry* 2003, 64 (suppl. 18):14-19, the results of clinical studies of immediate release and controlled release formulations of antidepressants were compared in relation to nausea leading to drug discontinuation. The author stated that "more stable pharmacokinetic profiles might be the cause for the low occurrence of nausea with some controlled-release newer antidepressants" but a "connection has not been proven."

According to Gerner et al., *Biol. Psychiatry,* 1998, 43:101 S, abstract 336 ("Gerner I"), "[b]upropion has been added to SSRIs for treatment of inadequate clinical response, SSRI sexual dysfunction, and for comorbid ADD and depression associated with [p]anic or [o]bsessive [c]ompulsive [d]isorders." See also Kennedy et al. *J. Clin. Psychiatry,* 2002, 63: 181-186 (study regarding the pharmacokinetic, therapeutic, and sexual dysfunction effects of combinations of bupropion SR with venlafaxine, paroxetine, or fluoxetine); Gerner et al., *Biol. Psychiatry,* 1998, 43:99 S, abstract 329 ("Gerner II"); Ashton et al., *J. Clin. Psychiatry,* 1998, 59(3):112-115 (study regarding the use of bupropion as an antidote for serotonin reuptake inhibitor (paroxetine, fluoxetine, sertraline, venlafaxine, or fluvoxamine) induced sexual dysfunction); Gitlin et al., *J. Sex & Marital Therapy* 2002, 28:131-138 (study regarding a bupropion sustained release formulation as a treatment for SSRI-induced sexual side effects). However, treatment of SSRI-induced sexual dysfunction with bupropion has not been proven to be effective. According to Sturpe et al., *J. Family Practice* August 2002, 51(8):1681, a double-blind placebo-controlled trial comparing augmentation therapy with bupropion showed equal improvement in sexual function to placebo. Furthermore, bupropion has increased seizure incidence compared with other antidepressants. *Gerner II,* supra (reporting on 3 cases of major motor seizures in previously seizure-free depressed patients after combining bupropion with fluoxetine or fluvoxamine); see also *Gerner I,* supra.

Studies suggest that between 29% and 46% of depressed patients fail to respond fully with antidepressant treatment of adequate dose and duration. Fava et al., *Psychiatr. Clin. North Am.,* 1996, 19(2):179-200; Fava et al., *Ann. Clin. Psychiatry,* 2003, 15(1): 17-22. Lam et al., *J. Clin. Psychiatry,* 2004, 65:337-340, reported the results of a clinical study comparing combining citalopram and bupropion SR versus switching to a monotherapy in patients with treatment-resistant depression. According to the authors, "[t]he results of this cohort study suggest that combining citalopram and bupropion SR is more effective than switching to a monotherapy."

U.S. Pat. No. 6,342,496 discloses bupropion metabolites for treating disorders ameliorated by inhibition of neuronal monoamine reuptake. The bupropion metabolite can be adjunctively administered with an additional pharmacologically active compound, such as an SSRI, 5-$HT_3$ inhibitor, or nicotine.

There is a need for methods of treating central nervous system disorders with fewer side effects than prior methods and which are effective in treatment-resistant patients.

There is also a need for methods of SSRI treatment that do not exhibit an initial reduction in 5-HT neuron activity and which do not exhibit a delay in SSRI therapeutic effect.

SUMMARY OF THE INVENTION

The present invention relates to a method of treating a central nervous system (CNS) disorder, such as a mood disorder (e.g., major depressive disorder) in a patient in need thereof, by administration of an effective amount of escitalopram (or a pharmaceutically acceptable salt thereof) and an effective amount of bupropion (or a pharmaceutically acceptable salt thereof). According to one preferred embodiment, the method involves daily administration of 4 mg of escitalopram or a pharmaceutically acceptable salt thereof and 150 mg of bupropion or a pharmaceutically acceptable salt thereof. In one embodiment, the escitalopram and bupropion may be co-administered or administered in a unitary oral dosage form containing both. In another related embodiment, the escitalopram and bupropion may be co-administered or administered in two or more oral dosage forms containing one or both. Preferably, the unitary dosage form or separate dosage forms are once daily formulations, i.e., one administration of each dosage form daily is sufficient to treat the desired CNS disorder. In still another embodiment, the escitalopram and bupropion may be administered sequentially. The low dose combination of escitalopram and bupropion has improved efficacy in the treatment of central nervous system disorders, such as major depressive disorder and anxiety disorders, with fewer side effects than prior formulations.

Examples of CNS disorders which can be treated include, but are not limited to, major depressive disorder, general anxiety disorder, social anxiety disorder, post traumatic stress disorder, panic attacks, acute stress disorder, eating disorders (such as bulimia, anorexia and obesity), phobias, dysthymia, premenstrual syndrome, premenstrual dysphoric disorder, cognitive disorders, impulse control disorders, attention deficit hyperactivity disorder and drug abuse. The combination of escitalopram and bupropion can also effectively treat patients who have failed to respond to initial treatment with a conventional SSRI, in particular patients with major depression disorder who have failed to respond to initial treatment with a conventional SSRI. The combination can further treat or reduce suicidal thoughts in a patient in need thereof, and improve disability free survival following stroke.

Another embodiment of the invention is a method of treating a patient suffering from nausea, insomnia, somnolence, increased sweating, fatigue, or a combination thereof due to treatment with an antidepressant other than a combination of bupropion or a pharmaceutically acceptable salt thereof and escitalopram or a pharmaceutically acceptable salt thereof. The method includes (a) discontinuing treatment with the antidepressant; and (b) treating the patient by co-administering an effective amount of bupropion or a pharmaceutically acceptable salt thereof and an effective amount of escitalopram or a pharmaceutically acceptable salt thereof. According to one embodiment, the antidepressant is a SSRI, such as escitalopram oxalate (e.g., an immediate release escitalopram oxalate formulation).

Yet another embodiment is a method for treating sexual dysfunction in a patient suffering from sexual dysfunction due to treatment with an antidepressant other than a combination of bupropion or a pharmaceutically acceptable salt thereof and escitalopram or a pharmaceutically acceptable salt thereof. The sexual dysfunction may be ejaculation disorder, anorgasmia, and/or decreased libido. The method includes (a) discontinuing treatment with the antidepressant;

and (b) treating the patient by co-administering bupropion or a pharmaceutically acceptable salt thereof and escitalopram or a pharmaceutically acceptable salt thereof. According to one embodiment, the antidepressant is a SSRI, such as escitalopram oxalate (e.g., an immediate release escitalopram oxalate formulation).

Yet another embodiment is a method of treating a patient suffering from treatment resistant depression by co-administering an effective amount of bupropion or a pharmaceutically acceptable salt thereof and an effective amount of escitalopram or a pharmaceutically acceptable salt thereof.

In another embodiment, the invention provides a method of reducing a delay in therapeutic efficacy following administration of escitalopram (i.e., after initiating treatment with escitalopram), comprising co-administering the escitalopram with bupropion. The method is preferably practiced by co-administering the SSRI and bupropion to a mammal, most preferably a human. Preferably, treatment is initiated with this co-administration regiment.

BRIEF DESCRIPTION OF DRAWINGS

FIG. 1 shows the mean change from baseline as measured by MADRS for each of the four treatment groups (placebo, 150 mg bupropion, 4 mg escitalopram, and a combination of 150 mg bupropion and 4 mg escitalopram) during 8 weeks of treatment.

FIG. 2 shows the mean change from baseline as measured by $HAMD_{24}$ for each of the four treatment groups (placebo, 150 mg bupropion, 4 mg escitalopram, and a combination of 150 mg bupropion and 4 mg escitalopram) during 8 weeks of treatment.

FIG. 3 shows the mean change from baseline as measured by $HAMD_{17}$ for each of the four treatment groups (placebo, 150 mg bupropion, 4 mg escitalopram, and a combination of 150 mg bupropion and 4 mg escitalopram) during 8 weeks of treatment.

DETAILED DESCRIPTION OF THE INVENTION

Definitions

The term "escitalopram" as used herein includes 1-[3-(dimethyl-amino)propyl]-1-(p-fluorophenyl)-5-phthalancarbonitrile preferably containing less than 3, 2, 1, 0.5, or 0.2% by weight of its R-enantiomer (based on 100% total weight of 1-[3-(dimethyl-amino)propyl]-1-(p-fluorophenyl)-5-phthalancarbonitrile), i.e., S-citalopram having an enantiomeric purity (by weight) of 97, 98, 99, 99.5, or 99.8%. Pharmaceutically acceptable salts of escitalopram include, but are not limited to, acid addition salts formed with organic and inorganic acids. Non-limiting examples of suitable organic acids are maleic, fumaric, benzoic, ascorbic, pamoic, succinic, oxalic, salicylic, methanesulfonic, ethanedisulfonic, acetic, propionic, tartaric, citric, gluconic, lactic, malic, mandelic, cinnamic, citraconic, aspartic, stearic, palmitic, itaconic, glycolic, p-amino-benzoic, glutamic, benzene sulfonic and theophylline acetic acid, as well as the 8-halotheophyllines, for example, 8-bromotheophylline. Non-limiting examples of suitable inorganic acids are hydrochloric, hydrobromic, sulfuric, sulfamic, phosphoric and nitric acids. Preferred pharmaceutically acceptable salts of escitalopram include, but are not limited to, escitalopram oxalate and escitalopram hydrobromide. The term "escitalopram" also includes polymorphs, hydrates, solvates, and amorphous forms of escitalopram and its pharmaceutically acceptable salts. Escitalopram and pharmaceutically acceptable salts thereof can be prepared as described in U.S. Pat. No. Re. 34,712 and 6,566,540 and International Publication Nos. WO 03/000672, WO 03/006449, WO 03/051861, and WO 2004/083197, each of which is hereby incorporated by reference. Crystals of escitalopram oxalate and escitalopram hydrobromide such as those described in International Publication No. WO 03/011278, U.S. Patent Application Publication No. 2004/0167209, and U.S. patent application Ser. Nos. 10/851,763 and 10/948,594, all of which are hereby incorporated by reference, can also be used. The comparative escitalopram "immediate release" tablets referred to herein are preferably those of United States Food and Drug Administration Approved New Drug Application No. 21-323 of equal amount (5, 10 and 20 mg escitalopram as oxalate).

Unless specified otherwise, all weight values of escitalopram salts are provided as the weight equivalent of escitalopram free base. For example, 4 mg escitalopram oxalate refers to an amount of escitalopram oxalate which is a molar equivalent to 4 mg escitalopram free base.

The term "bupropion" refers to (±)-1-(3-chlorophenyl)-2-[(1,1-dimethylethyl)amino]-1-propanone. Pharmaceutically acceptable salts of bupropion include, but are not limited to, acid addition salts formed with organic or inorganic acids, for example, hydrochloride, hydrobromide, sulphate, nitrate, phosphate, formate, mesylate, citrate, benzoate, fumarate, maleate and succinate. The term "bupropion" also includes polymorphs, hydrates, solvates, and amorphous forms of bupropion and its pharmaceutically acceptable salts. A preferred pharmaceutically acceptable salt of bupropion is bupropion hydrochloride. The comparative bupropion "immediate release" tablets referred to herein are preferably those of New Drug Application No. 018-644 of equal amount (50, 75, and 100 mg bupropion hydrochloride).

An "effective amount" means the amount of an active ingredient or a combination of active ingredients that, when administered to a mammal for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated. According to one embodiment of the present invention, an effective amount of escitalopram is an amount effective to treat a central nervous system (CNS) disorder, such as, major depressive disorder, general anxiety disorder, social anxiety disorder, post traumatic stress disorder, or panic attacks.

The term "pharmaceutically acceptable" generally means biologically or pharmacologically compatible for in vivo use in animals or humans, and preferably means approved by a regulatory agency of the Federal or a state government or listed in the U.S. Pharmacopoeia or other generally recognized pharmacopoeia for use in animals, and more particularly in humans.

As used herein, the term "treat" includes one or more of the following:
(a) relieving or alleviating at least one symptom of a disorder in a subject, including for example, central nervous system (CNS) disorders, (such as, mood disorders, major depressive disorder, general anxiety disorder, social anxiety disorder, post traumatic stress disorder, and panic attacks, including panic attacks);
(b) relieving or alleviating the intensity and/or duration of a manifestation of a disorder experienced by a subject including, but not limited to, those which are in response to a given stimulus (e.g., pressure, tissue injury, and cold temperature); and (c) arresting, delaying the onset (i.e., the period prior to clinical manifestation of a disorder) and/or reducing the risk of developing or worsening a disorder.

The term "panic attacks" includes, but is not limited to, any disease, which is associated with panic attacks including panic disorder, specific phobias, social phobia and agoraphobia in which panic attacks occur. These disorders are further defined in the Diagnostic and Statistical Manual of Mental Disorders 4$^{th}$ Ed.—Text Revision (DSM-IV-TR), A. Frances (ed.), American Psychiatric Association, Washington, D.C., 2000). A panic attack is a discrete period in which there is a sudden onset of intense apprehension, fearfulness or terror, often associated with feelings of impending doom. During the attack, symptoms such as palpitations, sweating, trembling, sensations of shortness of breath, feeling of choking, chest pain or discomfort, nausea, feeling dizzy, feelings of unreality, fear of losing control or going crazy, fear of dying, paresthesias and chills or hot flushes are present.

Panic disorders are characterized by recurrent unexpected panic attacks about which there is a persistent concern. Agoraphobia is anxiety about, or avoidance of, places or situations from which escape might be difficult or in which help may not be available in the event of a panic attack. Specific phobia and social phobia (together formerly simple phobia) are characterized by marked and persistent fear that is excessive or unreasonable, cued by the presence or anticipation of a specific object or situation (flying, heights, animals, seeing blood etc.) or social performance situations.

The disorders in which panic attacks occur are differentiated from each other by the predictability of the occurrence of the attacks, for example, in panic disorder the attacks are unpredictable and not associated with any particular event, whereas in specific phobia the attacks are triggered by specific stimuli.

The phrase "treatment of panic disorder" can include a reduction in the number or prevention of panic attacks and/or relief of the severity of the panic attacks.

The term "mood disorder" as used herein includes the mood disorders specified in the DSM-IV-TR, including, but not limited to, depressive disorders, such as major depressive disorder.

The term "anxiety disorder" as used herein includes the anxiety disorders specified in the DSM-IV-TR, including, but not limited to, panic disorder without agoraphobia, panic disorder with agoraphobia, social phobia (previously known as social anxiety disorder), obsessive-compulsive disorder, posttraumatic stress disorder, and generalized anxiety disorder.

Patients suffering from "treatment resistant depression" include (1) those who fail to respond to standard doses (i.e., significantly superior to placebo in double-blind studies) of antidepressants (such as SSRIs) administered continuously for a minimum duration of 6 weeks, and (2) those who fail to respond to standard doses of an antidepressant (such as an SSRI) (monotherapy) administered continuously for a minimum duration of 12 weeks. One criteria for determining whether a patient's depression is treatment resistant to an antidepressant is if a Clinical Global Impression-Improvement (CGI-I) score of 1 (very much improved) or 2 (much improved) is not achieved by the end of a 6, 8, or 12 week trial. The CGI-I scale is defined in Guy, W. (ed.): *ECDEU Assessment Manual for Psychopharmacology*, Revised, DHEW Pub. No. (ADM) 76-338, Rockville, Md., National Institute of Mental Health, 1976.

The terms "sustained release", "modified release", and "sustained or modified release" as used herein refer to the release of an active ingredient over an extended period of time leading to lower peak plasma concentrations and a prolonged $T_{max}$ as compared to immediate release formulations. These terms also include release over a period of time via a series of immediate release pulses. The pharmacokinetic profile for 100 mg Wellbutrin® tablets (immediate release bupropion hydrochloride tablets) shows a peak plasma concentration at approximately 1-2 hours following administration. The pharmacokinetic profile for 20 mg escitalopram oxalate tablets (immediate release tablets) show a peak plasma concentration at approximately 5 hours. (Physician's Desk Reference 2005, Thomson Healthcare; 59th ed. 2004).

By "pulsatile" is meant that a plurality of drug doses are released at spaced apart time intervals.

The term "bioavailability" refers to the rate and extent to which the active ingredient or active moiety, e.g., escitalopram, is absorbed from a drug product and becomes systematically available.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean a range of up to 10%, preferably up to 5%.

Combinations of Bupropion and Escitalopram

Oral dosages for use in the present invention preferably include about 75, 150, or 225 mg of bupropion hydrochloride and about 2.5, 4, 5, 10, 15, or 20 mg of escitalopram or a pharmaceutically acceptable salt thereof (such as escitalopram oxalate or escitalopram hydrobromide). These dosages can be in the form of a single oral dosage form or separate dosage forms administered simultaneously or sequentially. In another preferred embodiment, the oral dosages or oral dosage form preferably include about 75, 150, or 225 mg of bupropion hydrochloride and about 4, 8, 12, or 16 mg of escitalopram or a pharmaceutically acceptable salt thereof.

More preferred amounts of each component in the oral dosage include, but are not limited to, those shown in the table below.

| No. | Amount of Escitalopram (or Pharmaceutically Acceptable Salt Thereof) | Amount of Bupropion (or Pharmaceutically Acceptable Salt Thereof) |
|-----|---|---|
| 1 | 4 mg | 150 mg |
| 2 | 8 mg | 150 mg |

Unitary dosage forms containing both escitalopram and bupropion are preferably formulated so that the escitalopram and bupropion are not in contact with one another.

Modified Release Formulations

The dosage forms containing the bupropion and/or escitalopram may be formulated to provide modified release of the bupropion and immediate or modified release of the escitalopram. The modified release profiles for bupropion, escitalopram, or both can be achieved by sustained and pulsatile formulations.

Pulsatile Formulations

Pulsatile release profiles can be achieved with dosage forms that are closed, such as sealed capsules or tablets, which contain two or more drug-containing dosage units. The dosage form can include one, two, three, or four or more types of dosage units, each having a different drug release profile.

Each dosage unit can provide multi-phase release of the bupropion and/or escitalopram.

Preferably, a pulsatile dosage form includes at least two types of dosage units, and more preferably, includes two or three types of dosage units. For example, according to one embodiment, the first type of dosage unit releases drug substantially immediately following ingestion of the dosage form, the second type releases drug approximately 1 to 8 hours following ingestion, and the optional third type releases drug approximately 4 to 24 hours following ingestion.

According to another embodiment, more than 70% of the escitalopram and about 10 to 50% of the bupropion is released in a first pulse. The release of the remaining bupropion and any remaining escitalopram occurs in one or more pulses following the first pulse. The number of pulses and amount of the drugs released preferably result in a $T_{max}$ of from about 4 to about 35 hours for escitalopram and from about 4 to about 12 hours for bupropion.

Each dosage unit can be, for example, a tablet (e.g., compressed or molded), bead, or particle. Alternatively, the dosage units may be different layers on the dosage form (e.g., a multi-layered tablet). Suitable pulsatile systems are described in U.S. Pat. Nos. 6,217,904, 6,555,136, 6,793,936, 6,627,223, 6,372,254, 6,730,321, 6,500,457, 4,723,958, 5,840,329, 5,508,040, and 5,472,708 and U.S. Patent Application Publication Nos. 2003-124,196, 2004-028729, and 2003-0133978, all of which are hereby incorporated by reference.

The tablet dosage units can be of any size. According to one preferred embodiment, the tablets have a major diameter axis ranging from about 4.5 to about 15 mm. According to one embodiment, the dosage form (e.g., a capsule) contains two or three tablets.

Generally, the bead dosage units comprise an inert support with a drug coated thereon. The inert support can be, for example, a bead of sugar or microcrystalline cellulose. The drug can be coated on the inert support by methods known in the art.

The individual dosage units (such as beads and particles) can be compacted or compressed into a single tablet or capsule by methods known in the art.

Sustained Release Formulations

Sustained release profiles for a dosage form can be achieved by coatings and/or the use of the aforementioned beads, particles, and tablets as dosage units within the dosage form.

Dosage Units

As will be appreciated by those skilled in the art and as described in the pertinent texts and literature, a number of methods are available for preparing drug-containing tablets or other dosage units which provide a variety of drug release profiles. Such methods include coating a drug or drug-containing composition, increasing the drug's particle size, placing the drug within a matrix, and forming complexes of the drug with a suitable complexing agent.

The modified release dosage units for the pulsatile and sustained release formulations can be prepared, for example, by coating a drug or a drug-containing composition with one or more membrane coating materials, such as one or more polymeric materials. When a coating is used to provide delayed release dosage units, particularly preferred coating materials include, but are not limited to, bioerodible, gradually hydrolyzable and/or gradually water-soluble polymers. The "coating weight," or relative amount of coating material per dosage unit, generally dictates the time interval between ingestion and drug release.

Suitable membrane coating materials for effecting delayed release include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, cellulose ester-ether phthalate, hydroxypropylcellulose phthalate, alkali salts of cellulose acetate phthalate, alkaline earth salts of cellulose acetate phthalate, hydroxypropylmethyl cellulose hexahydrophthalate, cellulose acetate hexahydrophthalate, and carboxymethylcellulose sodium; acrylic acid polymers and copolymers preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate (such as a terpolymer of ethyl acrylate, methyl methacrylate and trimethylammonioethyl methacrylate chloride (available as Eudragit® RS from Röhm America L.L.C., of Piscataway, N.J.)); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac, ammoniated shellac, shellac-acetyl alcohol, and shellac n-butyl stearate.

In some cases, it may be desirable for a tablet, bead, or particle to provide for release of the drug in the colon, in which case polymeric or other materials are used that enable drug release within the colon. These may be selected from the aforementioned list, or other materials may be used as will be known to those skilled in the art of pharmaceutical formulation and drug delivery. For example, hydrocolloid gums may be effective to provide for colonic delivery, e.g., guar gum, locust gum, bena gum, gum tragacanth, and karaya gum (see, e.g., U.S. Pat. No. 5,656,294). Other materials suitable for effecting colonic drug delivery include polysaccharides, mucopolysaccharides, and related compounds, e.g., pectin, arabinogalactose, chitosan, chondroitin sulfate, dextran, galactomannan, and xylan.

The desired pulsatile profile may be achieved by a dosage form comprised of a plurality of tablets. The first tablet is provided with little or no coating material, the second tablet is provided with some degree of coating material, the third tablet is provided with even more coating material, and so on. Analogously, for encapsulated dosage forms in which the drug-containing dosage units are beads or particles, a first fraction of beads or particles is provided with little or no coating material, a second fraction is provided with some degree of coating material, the third faction is provided with even more coating material, and so on. For example, when the dosage form contains three tablets (or, analogously, three types of drug-containing particles or beads), the first tablet, which releases drug substantially immediately, may have a total coating weight of less than about 5% (preferably less than about 3%) (based on the total weight of the tablet), the second tablet may have a total coating weight in the range of approximately 5% to 30% (preferably 5% to 20%) and the third tablet, if present, may have a total coating weight in the range of approximately 15% to 40% (preferably 20% to 40%). The preferred coating weights for particular coating materials may be readily determined by those skilled in the art by evaluating individual release profiles for dosage units prepared with different quantities of various coating materials.

Alternatively, the delayed release dosage units, e.g., tablets or particles, may be formulated by dispersing the drug within a matrix (e.g., an insoluble matrix) of a suitable material such as an insoluble plastic, a hydrophilic polymer, or a fatty compound. The insoluble plastic matrices may be comprised of, for example, polyvinyl chloride or polyethylene. Hydrophilic polymers useful for providing a matrix for a delayed release dosage unit include, but are not limited to, those described above as suitable coating materials. Fatty compounds for use as a matrix material include, but are not limited to, waxes (e.g., carnauba wax) and glyceryl tristearate. Once the drug is mixed with the matrix material, the mixture can be compressed into tablets or processed into individual drug-containing particles.

The individual dosage units may be provided with colored coatings, with a single color used to identify a tablet or bead or particle fraction having a corresponding delayed release profile. That is, for example, a blue coating may be used for the immediate release tablet or bead or particle fraction, a red coating may be used for the "medium" release tablet or bead or particle fraction, and so on. In this way, errors during manufacture can be easily avoided. The color is introduced by incorporating a pharmaceutically acceptable colorant into the coating during coating preparation. The colorant may be either natural or synthetic. Natural colorants include, but are not limited to, pigments such as chlorophyll, anattenes, beta-carotene, alizarin, indigo, rutin, hesperidin, quercitin, carminic acid, and 6,6'-dibromoindigo. Synthetic colorants include, but are not limited to, dyes, including both acidic dyes and basic dyes, such as nitroso dyes, nitro dyes, azo dyes, oxazines, thiazines, pyrazolones, xanthenes, indigoids, anthraquinones, acridines, rosanilines, phthaleins, and quinolines.

For encapsulated tablets, the weight of each individual tablet in the capsule is typically in the range of about 50 mg to about 600 mg, preferably in the range of about 50 mg to about 450 mg, and more preferably in the range of about 60 mg to about 300 mg. The individual tablets can be prepared by methods known in the art. A preferred method for forming tablets herein is by direct compression of a powdered, crystalline or granular drug-containing composition, alone or in combination with diluents, binders, lubricants, disintegrants, colorants or the other excipients. Compressed tablets can also be prepared by wet-granulation or dry-granulation processes. Tablets may also be molded rather than compressed, starting with a moist material containing a suitable water-soluble lubricant. Drug-containing particles or beads may also be prepared by methods known in the art, such as with a fluid dispersion.

Coating procedures and equipment known in the art may be used to coat the dosage units, e.g., the drug-containing tablets, beads or particles. For example, a delayed release coating composition may be applied using a coating pan, or fluidized bed coating equipment. Materials, equipment and processes for preparing tablets, beads, drug particles, and delayed release dosage forms are described in *Pharmaceutical Dosage Forms: Tablets*, eds. Lieberman et al. (New York: Marcel Dekker, Inc., 1989), and Ansel et al., *Pharmaceutical Dosage Forms and Drug Delivery Systems*, 6$^{th}$ Ed. (Media, Pa.: Williams & Wilkins, 1995).

Optional components present in the individual drug-containing dosage units include, but are not limited to, diluents, binders, lubricants, disintegrants, stabilizers, surfactants, and coloring agents.

Diluents (also referred to as "fillers") are typically included to increase the bulk of a tablet so that a practical size is provided for compression. Suitable diluents include, but are not limited to, dicalcium phosphate dihydrate, calcium sulfate, lactose, cellulose, kaolin, mannitol, sodium chloride, dry starch, hydrolyzed starches, silicon dioxide, titanium oxide, alumina, talc, microcrystalline cellulose, powdered sugar, and mixtures thereof.

Binders are used to impart cohesive qualities to a tablet formulation, and thus ensure that a tablet remains intact after compression. Suitable binders include, but are not limited to, starch (including corn starch and pregelatinized starch), gelatin, sugars (including sucrose, glucose, dextrose, lactose and sorbitol), polyethylene glycol, waxes, natural and synthetic gums (e.g., acacia, tragacanth, sodium alginate, polyvinylpyrrolidone, celluloses, and Veegum), and synthetic polymers (such as polymethacrylates and polyvinylpyrrolidone), and mixtures thereof.

Lubricants are used to facilitate tablet manufacture. Examples of suitable lubricants include, but are not limited to, magnesium stearate, calcium stearate, stearic acid, glyceryl behenate, and polyethylene glycol. Preferably, a dosage unit contains no more than approximately 1 wt. % (relative to the weight of the dosage unit) of lubricant.

Disintegrants are used to facilitate tablet disintegration or "breakup" after administration. Suitable disintegrants include, but are not limited to, starches, clays, celluloses, algins, gums, crosslinked polymers, and mixtures thereof.

Stabilizers are used to inhibit or retard drug decomposition reactions which include, by way of example, oxidative reactions, such as those involving bupropion and pharmaceutically acceptable salts thereof (e.g., bupropion hydrochloride). Suitable stabilizers includes those described in U.S. Pat. Nos. 5,763,493, 5,731,000, and 5,358,970. The stabilizer can be an organic acid, a carboxylic acid, an acid salt of an amino acid, sodium metabisulphite, or a mixture thereof. Examples of acid salts of amino acids include, but are not limited to, hydrochloride salts such as cysteine hydrochloride, L-cysteine hydrochloride, glycine hydrochloride, and cystine dihydrochloride. Examples of other stabilizers include, but are not limited to, ascorbic acid, malic acid, isoascorbic acid, citric acid, and tartaric acid. According to one embodiment of the present invention, the dosage form contains sodium alginate as a stabilizer. According to another embodiment of the present invention, the dosage form is substantially or completely free of stabilizers.

Suitable surfactants include, but are not limited to, anionic, cationic, amphoteric, and nonionic surface active agents. Suitable anionic surfactants include, but are not limited to, those containing carboxylate, sulfonate and sulfate ions, associated with cations such as sodium, potassium and ammonium ions. Other suitable surfactants include, but are not limited to, long alkyl chain sulfonates and alkyl aryl sulfonates, such as sodium dodecylbenzene sulfonate; dialkyl sodium sulfosuccinates, such as sodium bis-(2-ethylhexyl)-sulfosuccinate; and alkyl sulfates such as sodium lauryl sulfate.

If desired, the tablets may also contain non-toxic auxiliary substances such as wetting or emulsifying agents, pH buffering agents, and preservatives.

As noted earlier herein, the individual drug tablets, beads or particles are, in one embodiment, contained within a closed capsule. The capsule material may be either hard or soft, and as will be appreciated by those skilled in the art of pharmaceutical science, typically comprises a tasteless, easily administered and water soluble compound such as gelatin, starch or cellulose. A preferred capsule material is gelatin. The capsules are preferably sealed, such as with gelatin bands. See, for example, *Remington: The Science and Practice of Pharmacy*, 20$^{th}$ Edition (Easton, Pa.: Mack Publishing Co., 2000), which describes materials and methods for preparing encapsulated pharmaceuticals designed to dissolve shortly after ingestion.

Dosage Form

A dosage form may also include one or more release modifiers in the form of polymeric coatings or matrices. A dosage form can also include one or more carriers, excipients, antiadherants, fillers, stabilizing agents, binders, colorants, glidants, and lubricants.

Depending upon the hydrophilic or hydrophobic nature of the matrix, it may be a material that swells upon contact with gastric fluid to a size that is large enough to promote retention in the stomach while the subject is in the digestive state. The digestive state is induced by food ingestion and begins with a rapid and profound change in the motor pattern of the upper gastrointestinal (GI) tract. The change consists of a reduction in the amplitude of the contractions that the stomach undergoes and a reduction in the pyloric opening to a partially closed state. The result is a sieving process that allows liquids and small particles to pass through the partially open pylorus while indigestible particles that are larger than the pylorus are retropelled and retained in the stomach. Biological fluids migrate through the matrix and dissolve the active ingredient which is released by diffusion through the matrix, which simultaneously modulates the release flow. The controlled-release matrix in these embodiments of the invention is therefore selected as one that can swell to a size large enough to be retropelled and thereby retained in the stomach, causing the prolonged release of the drug to occur in the stomach rather than in the intestines. Disclosures of oral dosage forms that swell to sizes that will prolong the residence time in the stomach are found in U.S. Pat. Nos. 5,007,790, 5,582,837, and 5,972,389, as well as International Publication Nos. WO 98/55107 and WO 96/26718. Each of the documents cited in this paragraph is incorporated herein by reference in its entirety.

The matrix may be composed of an insoluble hydrophilic polymer, such as a cellulose ester, carboxyvinyl ester, or acrylic or methacrylic ester. On contact with biological fluids, the hydrophilic matrix becomes hydrated and swells, forming a very dense network of polymers, through which the soluble active principles diffuse. Furthermore, lipids, in particular glyceryl esters, can be added in order to modulate the matrix swelling. These compositions can be obtained by granulation and then compression of the mixture formed of the polymer, active principles and various adjuvants.

Hydrophobic matrices can be composed of a lipid matrix agent of natural origin, for example beeswaxes, which is highly innocuous. These compositions can be obtained by granulation, by a wet or solvent route, and then compression involving high proportions of each of the constituents.

In general, swellable matrices contain binders that are water-swellable non-toxic polymers, swell in a dimensionally unrestricted manner upon imbibitions of water, and release the drug gradually over time. Examples of polymers meeting this description include, but are not limited to the following: cellulose polymers and their derivatives including, but not limited to, hydroxymethyl cellulose, hydroxyethyl cellulose, hydroxypropyl cellulose, hydroxypropylmethyl cellulose, carboxymethylcellulose, and microcrystalline cellulose polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, maltodextrins, poly (2-ethyl-2-oxazoline), poly(ethyleneimine), polyurethane hydrogels, and crosslinked polyacrylic acids and their derivatives. Further non-limiting examples are copolymers of the polymers listed above, including block copolymers and graft polymers. Specific examples of copolymers are PLURONIC® and TECTONIC®, which are polyethylene oxide-polypropylene oxide block copolymers and available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA.

Other suitable polymers for the matrices are poly(ethylene oxide), hydroxypropyl methyl cellulose, and combinations of poly(ethylene oxide) and hydroxypropyl methyl cellulose. A preferred polymer is hydroxypropyl methyl cellulose. In one embodiment, modified release formulations, such as a 24-hour modified release formulation, contain such polymers in amounts ranging from about 10% w/w to about 50% w/w, and preferably from about 15% to about 45% w/w.

The prolongation in the time of maximum plasma concentration values ($T_{max}$) as compared to immediate release, is related to the in vitro dissolution release rate of the drug. The in vitro dissolution release rate of the drug depends on the composition of the matrix. By using different cellulosic matrices, in-vitro release rates (drug dissolution of more than about 70% to about 80%) can be manipulated anywhere from about 4 hours to 24 hours. The formulations have a time of maximum plasma concentration (average $T_{max}$) ranging from between about 1 to about 35 hours for both drugs, preferably from about 4 to about 30 hours and an in vitro release rate of more than about 70% to about 80% in about 4 to about 24 hours. Preferably, the formulations have a release rate for escitalopram from about more than 80% in about 30 minutes to about 12 hours. More preferably, the formulations have a release rate of about 10% to about 40% within the first hour following entry into a use environment (such as the gastrointestinal tract) followed by extended release; and more preferably, the formulations have a release rate of more than 70% within the next 12 hours.

Tablets in accordance with this invention can be prepared by conventional mixing, comminution, and tabletting techniques that are well known in the pharmaceutical formulations industry. The modified-release tablet, for example, may be fabricated by direct compression by punches and dies fitted to a rotary tabletting press, ejection or compression molding, granulation followed by compression, or forming a paste and extruding the paste into a mold or cutting the extrudate into short lengths.

Fillers such as lactose (e.g., lactose monohydrate) are used to modify the dissolution pattern. When hydroxypropyl methylcellulose or ethyl cellulose are used, the dissolution rates can be much slower than the modified release rate targeted. The slow release is because hydrophobic matrix tablets that are formed release the drug by the mechanism of polymer erosion. Since the erosion from a hydrophobic matrix is very slow, the dissolution rate of the readily soluble active ingredient is also slow. Lactose, however, is also an important filler ingredient useful in improving the powder flow and compressibility for escitalopram and bupropion tablets.

When tablets are made by direct compression, the addition of lubricants may be helpful and is sometimes important to promote powder flow and to prevent capping of the tablet (the breaking off of a portion of the tablet) when the pressure is relieved. Useful lubricants include magnesium stearate, and hydrogenated vegetable oil (preferably hydrogenated and refined triglycerides of stearic and palmitic acids). In a preferred embodiment, the lubricant is magnesium stearate. For 24-hour release formulations, the magnesium stearate preferably is present in amounts ranging from about 0.5% w/w to about 3% w/w, and preferably from about 0.5% w/w to about 2% w/w. Additional excipients may be added to enhance tablet hardness, powder flowability, and tablet friability and to reduce adherence to the die wall.

EXAMPLES

The following examples illustrate the invention without limitation. All parts and percentages are given by weight unless otherwise indicated.

Example 1

Escitalopram Core and Modified Release Beads

Tables 1 and 2 show the formulation ingredients and weight percent ranges for the manufacture of escitalopram core and modified release beads, respectively. Each modified release bead is an escitalopram core bead coated with a modified release coating.

TABLE 1

Escitalopram Core Bead Formulation Ranges

| Ingredients | % w/w |
|---|---|
| Escitalopram Oxalate | 3.0-70.0 |
| Compritol ® 888* | 5.0-50.0 |
| Sorbitan Monostearate | 1.0-15.0 |
| Avicel ® PH 101** | 3.0-50.0 |
| PVP K-30*** | 1.0-7.0 |
| Talc, USP | 1.0-6.0 |
| Sorbitan Oleate | 3.0-15.0 |
| Total | 100.0 |

*Compritol ® 888 is glyceryl behenate (tribehenin) and is available from Gattefosse Corp. of Paramus, N.J.
**Avicel ® PH 101 is microcrystalline cellulose and is available from FMC Corporation of Philadelphia, PA.
***PVP K-30 is polyvinylpyrrolidone having a K-value of about 30.

TABLE 2

Escitalopram Modified Release Coating Formulation Ranges

| Ingredients | % w/w |
|---|---|
| Escitalopram Core Beads | 20-95 |
| Surelease ®**** | 2-40.0 |
| Purified Water | QS |
| Total | 100.0 |

****Surelease ® is an aqueous ethylcellulose dispersion and is available from Colorcon, Inc. of West Point, PA.

Escitalopram core beads (200 mg/g) having the formulation in Table 3 have been manufactured.

TABLE 3

Escitalopram Core Beads (200 mg/g)

| # | Ingredients | % w/w | Wt. in gms |
|---|---|---|---|
| 1. | Escitalopram Oxalate | 20.0 | 200 |
| 2. | Compritol ® 888 | 37.0 | 370 |
| 3. | Avicel ® PH 101 | 22.0 | 220 |
| 4. | PVP K-30 | 7.0 | 70 |
| 5. | Sorbitan Oleate | 10.0 | 100 |
| 6. | Talc, USP | 4.0 | 40 |
| | Total | 100.0 | 1000 |

The beads may be prepared by mixing ingredients 1-5 from Table 3 in a high shear granulator (Disona, Fluid Air, Chicago, Ill.). The granulated material is extruded with an extruder (Niro, Model E-140, Columbia Md.), and then spheronized into beads using a spheronizer (Niro Model S450, Columbia, Md.). The beads are optionally dried at 50° C. for up to 12 hours.

The escitalopram core beads from Table 3 have been coated with a modified release coating according to Table 4 (Profile I) or 5 (Profile II).

TABLE 4

Escitalopram Modified Release Beads (194.1 mg/g)

| Ingredients | % w/w |
|---|---|
| Escitalopram Core Bead, 200 mg/g | 97 |
| Surelease ® Dispersion (solid content) | 3 |
| Purified Water | QS |
| Total | 100.0 |

TABLE 5

Escitalopram Modified Release Beads (188.7 mg/g)

| Ingredients | % w/w |
|---|---|
| Escitalopram Core Bead, 200 mg/g | 94 |
| Surelease ® Dispersion (solid content) | 6 |
| Purified Water | QS |
| Total | 100.0 |

Example 2

Pulsatile Escitalopram Capsule Dosage Form

The escitalopram core and modified release beads described in Example 1 can be filled into capsules to deliver pulsatile release profiles. For example, predetermined weights of beads can be filled in a capsule using a capsule filling machine (MG-2, MG America, Fairfield, N.J.). The amounts of beads per capsule for a 4 mg strength pulsatile escitalopram capsule are shown in Table 6.

TABLE 6

Pulsative Escitalopram Capsule Dosage Formulations

| Profile | Core Bead (mg/cap) | Modified release bead 1 (mg/cap) | Modified release Bead 2 (mg/cap) |
|---|---|---|---|
| Single Pulse | 0 | 0 | 27.1 mg |
| Two Pulses | 6.4 mg | 0 | 20.3 mg |
| Three Pulses | 6.4 mg | 6.6 mg | 13.6 mg |

Capsules containing different amounts of beads of a given strength will generate different dissolution profiles. Also, different dose proportional strengths can be generated by using more beads, such for 5, 8, 10, 15, 16, 20, and 40 mg by the total fill weight.

Example 3

Bupropion Core and Modified Release Beads

Tables 7 and 8 show the formulation ingredients and weight percent ranges for the manufacture of bupropion core and modified release beads, respectively. Each modified release bead includes a bupropion core bead coated with a modified release coating.

TABLE 7

Bupropion Core Bead Formulation Ranges

| Ingredients | % w/w |
|---|---|
| Bupropion HCl | 3.0-70.0 |
| Compritol ® 888 | 5.0-50.0 |
| Sorbitan Monostearate | 1.0-15.0 |
| Avicel ® PH 101 | 3.0-50.0 |
| HPMC | 0-30.0 |
| PVP K-30 | 1.0-7.0 |
| Talc, USP | 1.0-6.0 |
| Sorbitan Oleate | 3.0-15.0 |
| Total | 100.0 |

TABLE 8

Bupropion Modified Release Coating Formulation Ranges

| Ingredients | % w/w |
|---|---|
| Bupropion HCl Core Beads | 20-95 |
| Eudragit ® | 5-40.0 |
| Purified Water | QS |
| Total | 100.0 |

Bupropion core beads (600 mg/g) having the formulation in Table 9 have been manufactured.

TABLE 9

Bupropion Core Beads (600 mg/g)

| # | Ingredients | % w/w | Wt. in gms |
|---|---|---|---|
| 1. | Bupropion HCl | 60.0 | 600 |
| 2. | Compritol ® 888 | 17.0 | 170 |
| 3. | Avicel ® PH 101 | 7.0 | 70 |
| 4. | PVP K-30 | 2.0 | 20 |
| 5. | Talc, USP | 4.0 | 40 |
| 6. | Sorbitan Oleate | 10.0 | 100 |
| | Total | 100.0 | 1000 |

The beads may be prepared by mixing ingredients 1-5 from Table 9 in a high shear granulator (Disona, Fluid Air, Chicago, Ill.). The granulated material is extruded with an extruder (Niro, Model E-140, Columbia Md.), and then spheronized into beads using a spheronizer (Niro Model S450, Columbia, Md.). The beads are optionally dried at 50° C. for up to 12 hours.

The bupropion core beads from Table 9 have been coated with a modified release coating according to Table 10 (Profile I) or Table 11 (Profile II).

TABLE 10

Bupropion Modified Release Beads (545.5 mg/g)

| Ingredients | % w/w |
|---|---|
| Bupropion Core Bead 600 mg/g | 90 |
| Eudragit ® RS/RL (95%:5%)* | 10 |
| Purified Water | QS |
| Total | 100.00 |

*Eudragit ® RS/RL (95%:5%) is a mixture containing 95% Eudragit ® RS and 5% Eudragit ® RL, both of which are available from Röhm America Inc. of Piscataway, N.J.

TABLE 11

Bupropion Modified Release Beads (500 mg/g)

| Ingredients | % w/w |
|---|---|
| Bupropion Core Bead 600 mg/g | 80 |
| Eudragit ® RS/RL (95%:5%) | 20 |
| Purified Water | QS |
| Total | 100.00 |

Example 4

Pulsatile Bupropion Capsule Dosage Form

Bupropion core and modified release beads described in Example 3 can be filled into capsules to deliver pulsatile release profiles. For example, predetermined weights of beads can be filled in a capsule using a capsule filling machine (MG-2, MG America, Fairfield, N.J.). The amounts of beads per capsule for a 150 mg strength pulsatile bupropion capsule are shown in Table 12.

TABLE 12

Pulsatile Bupropion Capsule Dosage Formulations

| Profile | Core Bead (mg/cap) | Modified release bead 1 (mg/cap) | Modified release Bead 2 (mg/cap) |
|---|---|---|---|
| Single Pulse | 250 mg | 0 | 0 |
| Two Pulses | 0 | 137.5 mg | 150 mg |
| Three Pulses | 0 | 0 | 300 mg |

Capsules containing different amounts of beads of a given strength will generate different dissolution profiles. Also, different dose proportional strengths can be generated by using more beads, such for 75 to 450 mg by the total fill weight.

Example 5

Pulsatile Escitalopram and Bupropion Capsule Dosage Form

A pulsatile capsule dosage form is prepared by packing a plurality of escitalopram beads and bupropion beads into a capsule. A pulsatile capsule dosage formulation for a 150 mg bupropion/4 mg strength escitalopram capsule is shown in Table 13.

TABLE 13

150 mg Bupropion/4 mg Escitalopram Pulsatile Capsule Dosage Form

| | Bupropion Core Pulse (mg/cap) | Bupropion MR Pulse 1 (mg/cap) | Bupropion MR Pulse 2 (mg/cap) | Escitalopram Core Pulse (mg/cap) | Escitalopram MR Pulse 1 (mg/cap) | Escitalopram MR Pulse 2 (mg/cap) |
|---|---|---|---|---|---|---|
| Two Pulses (One per API) (Capsule A) | 250 mg | 0 | 0 | 25.6 mg | 0 | 0 |
| Single MR Pulse (Capsule B) | 0 | 0 mg | 300 mg | 0 | 0 mg | 27.2 mg |
| Two MR Pulses (Capsule C) | 0 | 137.5 mg | 150 mg | 0 | 13.2 mg | 13.6 mg |

Multiple combinations of beads can be made to meet desired dissolution release profiles. The beads can be filled with a bead blend or multiple hoppers with an encapsulator (such as an MG-2, MG America, Fairfield, N.J.).

Dose proportional strengths can be prepared by altering the fill weight.

Example 6

Effects of the co-administration of bupropion and escitalopram on rat dorsal raphe nucleus serotonin neurons.

The effects of the combination of bupropion and escitalopram on rat dorsal raphe nucleus (DRN) 5-HT neurons was compared to the effects of the respective drugs given as monotherapies. Glass electrodes were lowered into the DRN 5-HT neurons were identified by their firing pattern and spike duration. Two days treatment with escitalopram (10 mg/kg) given to anesthetized rats using subcutaneously (s.c.) implanted minipumps markedly decreased spontaneous firing of DRN 5-HT neurons (control: 1.18 Hz+0.15 n=30; escitalopram: 0.35+0.06, n=27; p<0.001). Bupropion given once daily for two days (30 mg/kg, s.c.) with the last dose injected immediately prior to the experiment, did not significantly enhance the firing rate of DRN 5-HT neurons (1.54 Hz+0.17, n=26; NS). Administration of the combination of escitalopram and bupropion, given in the same doses and route as in the monotherapy experiments, significantly enhanced firing above bupropion alone (escitalopram+bupropion: 2.41 Hz+0.5, n=24; p<0.02).

The sensitivity of somatodendritic $5-HT_{1A}$ autoreceptors was assessed in rats treated with the combination of escitalopram and bupropion. The suppressant effect of LSD on the firing activity of 5-HT neurons was significantly attenuated by 72% in rats treated with escitalopram and bupropion for 2 days, indicating a desensitization of this autoreceptor.

This example shows that bupropion acted synergistically with escitalopram in the rat DRN to counteract inherent mechanistic delays of escitalopram in achieving therapeutic benefit.

Methods

The experiments were carried out in male Sprague Dawley rats (Charles River, St. Constant, Québec, Canada) weighing between 300 to 325 g being kept under standard laboratory conditions (12:12 light-dark cycle with access to food and water ad libitum). Rats were anaesthetized with chloral hydrate (400 mg/kg, i.p.) and mounted in a stereotaxic apparatus (David Kopf Instruments, Tujunga, Calif., USA). Supplemental doses (100 mg kg$^{-1}$, i.p.) were given to prevent any nociceptive reaction to pinching of the hind paw. Body temperature was maintained at 37° C. throughout the experiments utilizing a thermistor-controlled heating pad (Seabrook Medical Instruments, Inc., Saint-Hyacinthe, Quebec, Canada). Prior to electrophysiological recording, rats were inserted with a catheter in a lateral tail vein for systemic injection of drugs.

Rats received escitalopram oxalate administered through an osmotic minipump implanted subcutaneously, under halothane anaesthesia, which delivered 10 mg/kg/day. The recordings were carried out with the minipump in the animals. Bupropion hydrochloride was injected subcutaneously once a day at a dose of 30 mg/kg for 2 days with the last dose administered immediately prior to the electrophysiological experiments.

Extracellular unitary recordings of 5-HT neurons were conducted with single-barrelled glass micropipettes preloaded with fiberglass filaments (to facilitate filling) being pulled in a conventional manner, with the tips broken back to 1-3 μm and filled with a 2 M NaCl solution. Their impedance range was between 2 and 4 MΩ. A burr hole was drilled 1 mm anterior to lambda on midline for recording 5-HT neurons. Bleeding from disruption of the sagittal sinus was immediately stopped using bone wax. Serotonin neurons were recorded with micropipettes lowered at +1.0 mm interaural on midline. Spontaneously active 5-HT neurons of the dorsal raphe were identified using the following criteria: regular firing rate (0.5 2.5 Hz) and positive action potential of long duration (1.5-2.5 ms). Furthermore, these characteristic waveforms were encountered immediately for 1 mm starting immediately below the floor of the Sylvius aqueduct which corresponds to a period of electrical silence. Serotonin neurons were recorded for at least 1 min to establish basal firing rate.

Example 7

Depressed patients often do not improve quickly despite receiving known effective treatments because the benefits of antidepressant medications are delayed and because 60% of patients do not remit with the first antidepressant they receive. Further, some patients drop out of treatment before achieving remission. Methods for speeding and maximizing remission are needed. This pilot study assessed the possibility that combining medications having different mechanisms of action would both decrease time to remission and increase over-all remission rates in depressed outpatients.

Method 43 relatively treatment naive and physically healthy non-psychotic depressed outpatients were recruited. Following baseline physical tests, those who remained depressed and study eligible were given escitalopram plus bupropion in a rapid staggered dose escalation schedule such that tolerant patients were receiving escitalopram 40 mg/d plus bupropion 450 mg/d by day 15. Patients were evaluated weekly using the HAMD and CGI for four weeks and then biweekly for an additional four weeks.

All patients met inclusion and exclusion criteria (below).

Inclusion Criteria:
1) currently depressed (DSM IV major depression, dysthymia, or depression NOS)
2) HAMD-D (21-item)>9
3) agrees to participate Exclusion Criteria:
1) prior ineffective adequate trial on either study medication (≧4 weeks on either escitalopram ≧20 mg/d or bupropion ≧300 mg/d); ≧4 weeks on citalopram ≧40 mg/d also excludes
2) History suggesting increased risk for seizures (e.g., prior seizure as an adult, diagnosed seizure disorder, taking medication known to increase seizure risk, history of significant head trauma, history of bulimia or anorexia)
3) History of intolerance to either study medication unless patient and M.D. agree side effect is probably manageable
4) Alcohol and/or drug abuse/dependence during past year
5) Major medical problems that are not well-controlled (e.g., untreated hypertension or diabetes)
6) Bipolar I, Bipolar II
7) History of psychosis, or current psychosis
8) Pregnant or breast-feeding
9) Currently taking antidepressants or mood stabilizers, which is judged unwise to discontinue (occasional sleep medication or benzodiazepine for anxiety is allowed)
10) Premenopausal women not using known effective birth control
11) Not currently depressed (whether considered due to current treatment or not)
12) Active suicidal risk*

*History of suicide attempts will be evaluated on a case by case basis

Following initial history using the SCID, determination of study eligibility, and other baseline measures (HAMD, CGI, BDI, PGI, and SCL-90), and explanation of the study, blood was drawn for routine laboratory determinations, EKG and urine were obtained and a physical examination completed. Patients were re-evaluated in one week (no placebo) and if still study eligible were started on study medication according to the schedule below. They were seen weekly with HAMD, CGI, BDI and PGI (a patient-rated CGI) for four weeks and biweekly for four weeks at which time final outcome was determined. In addition, SCL-90 was obtained at the re-evaluation just prior to giving first study medication, at week 4 and 8 visits. Patients were called on the telephone mid-week for the first two weeks (i.e., during rapid dose raises), and patients were encouraged to telephone at any time should they experience difficult physical problems. Adverse events (AE's) were collected at each visit on an AE form on which one line was devoted to each reported AE. One column in each row indicated the AE, its general code, whether it predated study medication, if predating whether it had become worse, a date for onset and offset, severity, degree to which the clinician attributed the AE to study medication, what was done about the AE, and whether it resolved or continued.

| Dose Schedule (assuming patient tolerance) | | | |
|---|---|---|---|
| Study Day | Escitalopram | Bupropion-SR* | Bupropion-XL** |
| 1-2 | 10 | — | — |
| 3-4 | 10 | 100 | 150 |
| 5-6 | 20 | 100 | 150 |
| 7-8 | 20 | 200 | 300 |
| 9-10 | 30 | 200 | 300 |
| 11-14 | 40 | 300 | 300 |
| 15ff | 40 | 400 | 450 |

*first 17 patients
**last 21 patients

Clinicians were encouraged to delay dose increases or decrease dose if presumed side effects so dictated.

Results

Five patients did not receive study medication. Of 38 who did, 12 (31%) were remitted (HAMD<8) by two weeks, and 23 (61%) were remitted by eight weeks. 9 (24%) patients did not complete the study, 7 due to Adverse Events (AE's), including dizziness and daytime sedation (two patients each), and hives, 'hyper', bloating, and 'spacey' (one patient each). While 11 (29%) of patients experienced at least one severe AE, the majority improving by end of study.

The 38 patients who received study medication included 24 (63%) women, 63% were Caucasian, mean age was 39±12 (range, 21-64) and mean HAMD was 15±4. 71% (n=27) had current major depression, 15 (40%) dysthymic disorder, and 5 (13%) depression NOS. In addition, 8% had panic disorder, 5% social phobia, 8% OCD, 3% PTSD, 8% an eating disorder, and 11% past alcohol abuse. An additional patient had body dysmorphic disorder.

23 (61%) had remitted (17-item HAMD≦7) by study end. 12 (31%) had remitted in week 1 or week 2. Mean 17-item HAMD had dropped from 15±4 to 11±6 at week 2 and 7±7 at end of study.

Nine (24%) patients did not complete the study. Two drop outs attributed their noncompletion to reasons other than AE's, one finding himself unable to make appointments (without stated AE's) and the other due to lack of benefit (after completing 7 weeks with AE she had tolerated until that point). In 7 patients, noncompletion was attributed to AE□s. These included dizziness and daytime sedation (each experience by two patients), and hives, "hyper", bloating, and 'spacey' (each experienced by one patient). Other AE's experienced during the study together with severity are given in Tables 14-19. Table 14 gives information about worst AE and for worst AE in each of several commonly experienced categories, including overstimulation, gi, sleep, sexual and mental. Tables 16-20 breaks down each of these categories, while Table 15 presents miscellaneous other AE's that do not fit into any category. Each table shows a line for number (and percent) of patients having that side effect with its worst severity, number and % having that side effect at the end of the study, and number/% having a change in severity of each side effect or side effect category. I realize this is way too much, but you asked for it, so you get it.

Mean final dose was 30±13 mg/d for escitalopram, and 347±124 for bupropion. Eleven (29%) followed the protocol dosing schedule and completed the study on maximal dose of both medications. A further 6 (16%) patients followed the protocol dose increases as long as they remained in the study, but did not complete the full eight weeks. Another 5 (13%) got to study maximal dose according to the dosing schedule but later had their dose reduced, while 4 (11%) of patients reached the maximal doses but via delayed escalation. Finally, 12 (32%) completed the study having not reached study maximal doses. In all, 19 (50%) reached study maximal doses of both drugs, and 17 (45%) were at maximal dose at study end. Of note, is that one patient came for his week 8 visit stating he had increased his bupropion to 600 mg/d, so end dose of bupropion ranges from 0 mg/d to 600 mg/d, and for escitalopram from 0 mg/d to 40 mg/d, as two patients was unable to tolerate one of the medications and ended the study only on the other (one each for escitalopram and bupropion).

TABLE 14

Severity of AE's in Double Therapy Study (N = 38)

| Worst AE | None | Mild | Moderate | Severe |
|---|---|---|---|---|
| Worst | 3% (1) | 13% (5) | 55% (21) | 29% (11) |
| End Study | 18% (7) | 42% (16) | 32% (12) | 8% (3) |
| Change* | 46% (17) | 27% (10) | 24% (9) | 3% (1) |
| Any Overstimulation | | | | |
| Worst | 39% (15) | 53% (20) | 8% (3) | — |
| EndStudy | 71% (27) | 21% (8) | 8% (3) | — |
| Change* | 48% (11) | 52% (13) | — | — |
| Any GI Disturbance | | | | |
| Worst | 42% (16) | 35% (9) | 29% (11) | 5% (2) |
| End Study | 74% (28) | 16% (6) | 11% (4) | — |
| Change* | 34% (8) | 27% (6) | 32% (7) | 5% (1) |
| Any Sleep Disturbance | | | | |
| Worst | 34% (13) | 24% (9) | 36% (10) | 16% (6) |
| End Study | 47% (18) | 34% (13) | 13% (5) | 5% (2) |
| Change* | 50% (13) | 31% (8) | 19% (5) | — |
| Any Sexual Disturbance | | | | |
| Worst | 76% (29) | 8% (3) | 11% (4) | 5% (2) |
| EndStudy | 89% (34) | 5% (2) | 3% (1) | 3% (1) |
| Change* | 33% (3) | 44% (4) | 11% (1) | 11% (1) |
| Any Mental Disturbance | | | | |
| Worst | 45% (17) | 24% (9) | 18% (7) | 13% (5) |
| EndStudy | 82% (31) | 13% (5) | 5% (2) | — |
| Change* | 24% (5) | 29% (6) | 33% (7) | 14% (3) |

TABLE 15

Miscellaneous General AE's

| | None | Mild | Moderate | Severe |
|---|---|---|---|---|
| Hives | | | | |
| Worst | 95% (36) | — | 5% (2) | — |
| End Study | 95% (36) | — | 5% (2) | — |
| Change* | 100% (2) | — | — | — |
| Low Energy | | | | |
| Worst | 79% (30) | 13% (5) | 3% (1) | 5% (5) |
| End Study | 92% (35) | 5% (2) | — | 3% (1) |
| Change* | 25% (2) | 63% (5) | — | 13% (1) |
| Flushing | | | | |
| Worst | 97% (37) | 3% (1) | — | — |
| End Study | 100% (38) | — | — | — |
| Change* | — | 100% (1) | — | — |
| Sweating | | | | |
| Worst | 84% (32) | 3% (1) | 13% (5) | — |
| End Study | 84% (32) | 3% (1) | 13% (5) | — |
| Change* | 100% (6) | — | — | — |
| Yawning | | | | |
| Worst | 92% (35) | — | 8% (3) | — |
| End Study | 92% (35) | — | 8% (3) | — |

TABLE 15-continued

Miscellaneous General AE's

| | None | Mild | Moderate | Severe |
|---|---|---|---|---|
| Change* | 100% (3) | — | — | — |
| Urinary Hesitancy | | | | |
| Worst | 97% (1) | 3% (1) | — | — |
| End Study | 97% (1) | 3% (1) | — | — |
| Change* | 100% (1) | — | — | — |

TABLE 16

Overstimulation AEs

| | None | Mild | Moderate | Severe |
|---|---|---|---|---|
| Feeling 'revved up' | | | | |
| Worst | 76% (29) | 8% (3) | 16% (6) | — |
| End Study | 97% (37) | 3% (1) | — | — |
| Change* | 11% (1) | 22% (2) | 67% (6) | — |
| Twitching | | | | |
| Worst | 95% (36) | 3% (1) | 3% (1) | — |
| End Study | 97% (37) | 3% (1) | — | — |
| Change* | 50% (1) | — | 50% (1) | — |
| Muscle Tension | | | | |
| Worst | 87% (33) | 5% (2) | 5% (2) | 3% (1) |
| End Study | 97% (37) | — | 3% (1) | — |
| Change* | 20% (1) | 40% (2) | 20% (1) | 20% (1) |
| Jaw Clenching | | | | |
| Worst | 95% (36) | 3% (1) | 3% (1) | — |
| End Study | 97% (37) | — | 3% (1) | — |
| Change* | 50% (1) | 50% (1) | — | — |
| Tremor | | | | |
| Worst | 79% (30) | 18% (7) | 3% (1) | — |
| End Study | 87% (33) | 13% (5) | — | — |
| Change* | 50% (4) | 50% (4) | — | — |
| Anxiety (treatment emergent) | | | | |
| Worst | 95% (36) | 3% (1) | 3% (1) | — |
| End Study | 95% (36) | 3% (1) | 3% (1) | — |
| Change* | 100% (2) | — | — | — |
| Irritability (treatment emergent) | | | | |
| Worst | 97% (37) | — | 3% (1) | — |
| End Study | 97% (37) | — | 3% (1) | — |
| Change* | 100% (1) | — | — | — |
| Restless Legs | | | | |
| Worst | 92% (35) | 8% (3) | — | — |
| End Study | 95% (36) | 5% (2) | — | — |
| Change* | 67% (2) | 33% (1) | — | — |

TABLE 17

GI Disturbance

| | None | Mild | Moderate | Severe |
|---|---|---|---|---|
| Nausea | | | | |
| Worst | 74% (28) | 16% (6) | 5% (2) | 5% (2) |
| End Study | 89% (34) | 8% (3) | 3% (1) | — |
| Change* | 40% (4) | 30% (3) | 10% (1) | 20% (2) |
| Vomiting | | | | |
| Worst | 97% (37) | 3% (1) | — | — |

TABLE 17-continued

GI Disturbance

|  | None | Mild | Moderate | Severe |
|---|---|---|---|---|
| End Study | 100% (38) | — | — | — |
| Change* | — | 100% (1) | — | — |
| Decreased Appetite |  |  |  |  |
| Worst | 84% (32) | 13% (5) | 3% (1) | — |
| End Study | 97% (37) | 3% (1) | — | — |
| Change* | 17% (1) | 67% (4) | 17% (1) | — |
| Bloating |  |  |  |  |
| Worst | 95% (36) | — | 5% (2) | — |
| End Study | 100% (38) | — | — | — |
| Change* | — | — | 100% (2) | — |
| Diarrhea |  |  |  |  |
| Worst | 97% (37) | 3% (1) | — | — |
| End Study | 100% (38) | — | — | — |
| Change* | — | 100% (1) | — | — |
| Frequent Bowel Movements |  |  |  |  |
| Worst | 95% (36) | 5% (2) | — | — |
| End Study | 97% (37) | 3% (1) | — | — |
| Change* | 50% (1) | 50% (1) | — | — |
| Constipation |  |  |  |  |
| Worst | 89 (34) | 3% (1) | 8% (3) | — |
| End Study | 95% (36) | — | 5% (2) | — |
| Change* | 50% (2) | 25% (1) | 25% (1) | — |
| Dry Mouth |  |  |  |  |
| Worst | 68% (26) | 212% (8) | 8% (3) | 3% (1) |
| End Study | 87% (33) | 11% (4) | 3% (1) | — |
| Change* | 42% (5) | 33% (4) | 17% (2) | 8% (1) |
| Abdominal Pain |  |  |  |  |
| Worst | 97% (37) | — | 3% (1) | — |
| End Study | 100% (38) | — | — | — |
| Change* | — | — | 100% (1) | — |
| Metallic Taste |  |  |  |  |
| Worst | 97% (37) | — | 3% (1) | — |
| End Study | 97% (37) | — | 3% (1) | — |
| Change* | 100% (1) | — | — | — |

TABLE 18

Sleep Disturbance

|  | None | Mild | Moderate | Severe |
|---|---|---|---|---|
| Insomnia |  |  |  |  |
| Worst | 53% (20) | 24% (9) | 21% (8) | 3% (1) |
| End Study | 66% (25) | 24% (9) | 8% (3) | 3% (1) |
| Change* | 56% (10) | 33% (6) | 11% (2) | — |
| Sedation/Daytime Sleepiness |  |  |  |  |
| Worst | 68% (26) | 8% (3) | 11% (4) | 13% (5) |
| End Study | 82% (31) | 11% (4) | 5% (2) | 3% (1) |
| Change* | 43% (5) | 8% (1) | 33% (4) | 17% (2) |
| Increased/Vivid Dreams |  |  |  |  |
| Worst | 92% (35) | 3% (1) | 5% (2) | — |
| End Study | 92% (35) | 5% (2) | 3% (1) | 0 |
| Change* | 67% (2) | 33% (1) | — | — |

TABLE 19

Sexual Dysfunction

Delayed Orgasm

| | | | | |
|---|---|---|---|---|
| Worst | 79% (30) | 8% (3) | 8% (3) | 5% (2) |
| End Study | 89% (34) | 5% (2) | 3% (1) | 3% (1) |
| Change* | 38% (3) | 38% (3) | 13% (1) | 13% (1) |

Decreased Libido

| | | | | |
|---|---|---|---|---|
| Worst | 92% (35) | 5% (2) | 3% (1) | — |
| End Study | 95% (36) | 3% (1) | 3% (1) | — |
| Change* | 67% (2) | 33% (1) | — | — |

Erectile Dysfunction

| | | | | |
|---|---|---|---|---|
| Worst | 97% (37) | — | 3% (1) | — |
| End Study | 100% (38) | — | — | — |
| Change* | — | — | 100% (1) | — |

TABLE 20

Mental Problems

|  | None | Mild | Moderate | Severe |
|---|---|---|---|---|
| Headache |  |  |  |  |
| Worst | 74% (28) | 5% (2) | 13% (5) | 8% (3) |
| End Study | 95% (36) | 3% (1) | 3% (1) | — |
| Change* | 20% (2) | 10% (1) | 40% (4) | 30% (3) |
| Trouble Thinking, Remembering, Finding Words |  |  |  |  |
| Worst | 87% (33) | 8% (3) | 5% (2) | — |
| End Study | 92% (35) | 5% (2) | 3% (1) | — |
| Change* | 60% (3) | 20% (1) | 20% (1) | — |
| Spacey |  |  |  |  |
| Worst | 89% (34) | 8% (3) | 3% (1) | — |
| End Study | 97% (37) | 3% (1) | — | — |
| Change* | 25% (1) | 50% (2) | 25% (1) | — |
| Dizzy |  |  |  |  |
| Worst | 82% (31) | 5% (2) | 5% (2) | 8% (3) |
| End Study | 95% (36) | 5% (2) | — | — |
| Change* | 29% (2) | 57% (4) | 14% (1) | — |
| Paresthesias |  |  |  |  |
| Worst | 92% (35) | 3% (1) | 5% (2) | — |
| End Study | 100% (38) | — | — | — |
| Change* | — | 33% (1) | 67% (2) | — |

Example 8

Fixed Dose Comparison of Escitalopram Combination in Adult Patients with Major Depressive Disorder The present study evaluates the efficacy, safety, and tolerability of escitalopram/bupropion combination treatment relative to its component monotherapies, and to placebo in patients with major depressive disorder (MDD).

Method

This clinical study is conducted as a double-blind, randomized, fixed-dose, multicenter, parallel-group study in outpatients as shown in the Figure below:

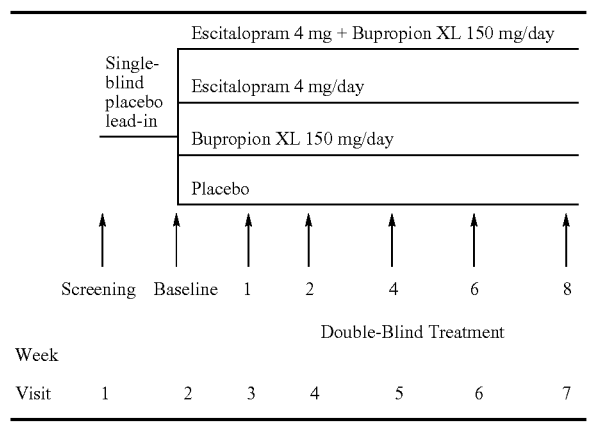

The study consists of a one-week single-blind placebo lead-in period followed by an 8 week double-blind treatment period. Approximately 135 patients are randomized to each of four treatment groups (placebo, escitalopram oxalate 4 mg, bupropion hydrochloride 150 mg, or escitalopram oxalate 4 mg/bupropion hydrochloride 150 mg), for a total of 558 patients.

A randomized, double-blind, fixed-dose, multicenter, parallel-group study is conducted in outpatients with MDD. Patients who meet eligibility criteria at Screening (Visit 1) enter a one-week, single-blind, lead-in period of placebo treatment. Patients who complete the lead-in period and continue to meet all entry criteria at Baseline (Visit 2) are randomly assigned to 8 weeks of double-blind treatment with either placebo, escitalopram 4 mg, bupropion XL 150 mg, or escitalopram 4 mg/bupropion XL 150 mg combination. Assignment to a treatment group is according to a computer-generated randomization schedule.

After Baseline (Visit 2), study visits are conducted at the end of Weeks 1 (Visit 3), 2 (Visit 4), 4 (Visit 5), 6 (Visit 6), and 8 (Visit 7). If necessary, study visits are conducted up to 3 days before or after the final day of the study week. The Mini International Neuropsychiatric Interview (MINI) is administered at Visit 1 only and are considered a source document.

The following primary efficacy assessments are performed at patient visits: Montgomery Asberg Depression Rating Scale (MADRS)— This clinician rated scale is be administered at Visits 1 through 7, including early termination, with regard to the patient's depressive symptomatology during the past week. Patients are rated on 10 items assessing feelings of sadness, lassitude, pessimism, inner tension, suicidality, reduced sleep or appetite, difficulty in concentration, and lack of interest. Each item is scored on a 7 point scale with a score of 0 reflecting no symptoms and a score of 6 reflecting symptoms of maximum severity.

The following secondary efficacy assessments are performed at patient visits: Hamilton Depression Rating Scale (HAMD-24)—This clinician rated scale is administered at Visits 1 through 7, including early termination. This 24-item scale rates the patient's depressive state based on feelings of depression, guilt suicidality, anxiety, agitation, helplessness, hopelessness, worthlessness, or depersonalization/derealization, his/her level of insight, his/her patterns of insomnia, loss of interest in work and other activities, weight loss, hypochondriasis, psychomotor retardation, or the presence of paranoid, obsessive-compulsive, genital, or somatic symptoms, and diurnal variation in the presence of symptoms.

The following additional efficacy assessments are performed at patient visits: Clinical Global Impressions-Severity (CGI-S)— The CGI-S is a clinician rated scale performed at Visits 1 through 7, including early termination. This scale rates the severity of the patient's current state of mental illness based on the investigator's clinical opinion with regard to a patient population with MDD. The patient is rated on a scale of 1 to 7 with 1 being normal and 7 being a patient who was among the most extremely ill. Clinical Global Impressions-Improvement (CGI-I)—The CGI-I is a clinician rated scale performed at Visits 3 through 7, including early termination. Based on the investigator's clinical opinion, this scale rates the total improvement or worsening in the patient's mental illness from his/her baseline assessment, regardless of whether or not the investigator considered it due to drug treatment. The patient is rated on a scale from 1 to 7 with 1 being very much improved and 7 being very much worse. Hamilton Anxiety Scale (HAMA)—This clinician rated scale is administered at Visits 2, 5, and 7, including early termination. This 14-item scale rates the patient's level of anxiety based on feelings of anxiousness, tension, and depression; any phobias, sleep disturbance, or difficulty in concentrating; the presence of genitourinary, cardiovascular, respiratory, autonomic or somatic symptoms; and the interviewer's assessment of the patient's appearance and behavior during the interview. Each item is scored on a 5 point scale with 0 reflecting no symptoms and 4 reflecting symptoms of maximum severity. Quality of Life (QOL)—The self-rated questionnaire is completed at Visits 2, 5, and 7, or early termination. This 16 item patient-rated scale assesses an individual's perceived quality of life and satisfaction in multiple domains of functioning. Five-point item scores are aggregated, with higher scores indicative of greater enjoyment or satisfaction in each domain.

Safety assessments are made of the patients by a physician at every visit and the evaluation documented. At each visit beginning with Visit 2, patients are queried regarding any adverse events (AEs) since the last visit. Study site personnel record all pertinent information in the electronic Case Report Forms (eCRF). Patients are asked to volunteer information concerning AEs with non-leading question such as "How do you feel?" AEs are collected at Visit 2 and all subsequent visits including early termination.

Blood and urine specimens are collected at Visits 1 and 7, or early termination. Women of childbearing potential are required to have a serum pregnancy test at Visit 1. Specimens are submitted for analysis as per the instructions of the central laboratory. The following parameters are measured: Hematology/Chemistry/Urinalysis and other standard laboratory tests. The following tests are performed at Visit 1 only: serum β-HCG pregnancy test (for women of child bearing potential), urine drug screen, and TSH.

Pulse rate and systolic and diastolic blood pressure (after the patient has been sitting for 5 minutes) are recorded at Visits 1 through 7, including early termination. These measures are also obtained 1 minute after the patient stands up at each visit, including early termination. Body weight is recorded at every visit. Whenever possible, the patient's weight is measured at the same time of day, with the patient either consistently fasting or consistently non-fasting. Patients wear their usual indoor clothing but take off their jacket and shoes. Only a well-calibrated balance beam scale is used. Height is recorded at Visit 1 only.

A complete physical examination is performed at Visits 1 and 7, or early termination. The physical examination is performed by a physician or by a health care professional trained and licensed to perform physical examinations.

A 12-lead electrocardiogram (ECG) is recorded at Visits 1 and 7, or early termination, and when medically indicated. ECGs are obtained and analyzed as per the instructions of the central ECG laboratory. The interpretation of the ECG are the responsibility of the physician at the study center.

The Arizona Sexual Experiences Scale (ASEX) is completed at Visits 2 and 7, or early termination. Different versions are used for males and females. This 5 item patient-rated scale assesses sexual experiences with respect to libido, psychological and physiological arousal, ability to attain orgasm, and satisfaction with orgasm. Each item is scored on a 6 point scale with higher numbers indicating greater sexual dysfunction.

Any clinical findings in the final examination, or at premature discontinuation for any reason, including clinically significant laboratory abnormalities, are followed until the condition returns to pre-study status or can be explained as being unrelated to the study drug. A follow-up visit is scheduled within 28 days of termination, if necessary.

Dosing: For the single-blind lead-in period, patients are supplied with placebo capsules. For the double-blind period, identical appearing capsules are supplied which contain placebo, escitalopram 4 mg, or bupropion extended-release 150 mg. Medication are supplied in blister cards, each containing 20 capsules arranged in two rows of 10 capsules.

All study medication is administered as a single daily dose throughout the study, preferably at the same time each evening starting on the day the medication is dispensed to the patient. Dosing is subsequently be switched to morning, if preferred. At each visit, patients are instructed to take 2 capsules daily, one from Row 1 and one from Row 2. Patients are instructed to return all unused medication at each study visit. Patients who meet eligibility criteria at Visit 1 are dispensed one blister card containing 20 placebo capsules. Patients are instructed to take two capsules daily as a single dose beginning on the day study medication is dispensed. Patients who meet all eligibility criteria at Visit 2 are assigned a randomization number and dispensed the corresponding blister card for Week 1 of treatment as shown in the Figure below:

| Double-Blind Blister Card Configurations | | | | | | | | | | |
|---|---|---|---|---|---|---|---|---|---|---|
| | Day | | | | | | | | | |
| | 1 | 2 | 3 | 4 | 5 | 6 | 7 | 8 | 9 | 10 |
| Treatment Group: Placebo | | | | | | | | | | |
| Row 1 | Pbo | Pbo | Pbo | Pbo | Pbo | Pbo | Pbo | Pbo | Pbo | Pbo |
| Row 2 | Pbo | Pbo | Pbo | Pbo | Pbo | Pbo | Pbo | Pbo | Pbo | Pbo |
| Treatment Group: Escitalopram | | | | | | | | | | |
| Row 1 | E4 | E4 | E4 | E4 | E4 | E4 | E4 | E4 | E4 | E4 |
| Row 2 | Pbo | Pbo | Pbo | Pbo | Pbo | Pbo | Pbo | Pbo | Pbo | Pbo |
| Treatment Group: Bupropion | | | | | | | | | | |
| Row 1 | B150 | B150 | B150 | B150 | B150 | B150 | B150 | B150 | B150 | B150 |
| Row 2 | Pbo | Pbo | Pbo | Pbo | Pbo | Pbo | Pbo | Pbo | Pbo | Pbo |
| Treatment Group: Escitalopram/Bupropion | | | | | | | | | | |
| Row 1 | E4 | E4 | E4 | E4 | E4 | E4 | E4 | E4 | E4 | E4 |
| Row 2 | B150 | B150 | B150 | B150 | B150 | B150 | B150 | B150 | B150 | B150 |

Note:
Pbo: placebo,
E4: escitalopram 4 mg,
B150: bupropion XL150 mg

Patients are assigned the lowest randomization number available at the site. Patients are instructed to take two capsules daily as a single dose beginning on the day study medication is dispensed. In accordance with their assigned treatment group, patients receive placebo, 4 mg escitalopram, 150 mg bupropion, or 4 mg escitalopram and 150 mg bupropion per day.

At Visit 3, patients are dispensed one blister card for Week 2 of treatment. At Visits 4, 5, and 6, patients are dispensed two blister cards for Weeks 3-4, 5-6, and 7-8 of treatment, respectively. Patients are instructed to continue taking two capsules daily as a single dose. In accordance with their assigned treatment group, patients receive placebo, 4 mg escitalopram, 150 bupropion, or 4 mg escitalopram and 150 mg bupropion per day.

Efficacy: All efficacy analyses are based on the Intent-to-Treat (ITT) Population. All statistical tests are two-sided hypothesis tests performed at the 5% level of significance.

All efficacy analyses are performed using both the Last Observation Carried Forward (LOCF) and the Observed Cases (OC) approach. In these analyses, the last observed value before a post-baseline missing value are carried forward to impute the missing value. If the missing value occurs at Week 1, the Baseline (Visit 2) value are carried forward to Week 1 only if the patient has another non-missing value post-baseline. For OC analyses, only observed values are used.

Descriptive statistics are presented by visit and treatment group using both LOCF and OC approaches.

For the Primary Efficacy Parameter, change from Baseline (Visit 2) to Week 8 in MADRS total score is used as the primary efficacy parameter. The primary analysis is performed using the LOCF approach. Three primary comparisons between the escitalopram/bupropion combination group relative to each of the three other groups (placebo, escitalopram, or bupropion) are performed using an ANCOVA model with the treatment group and center as factors and the baseline MADRS score as a covariate.

The Shapiro-Wilk test is used to examine the normality of the residuals from the above ANCOVA model. If the assumption of normality of the residuals from the above ANCOVA model is rejected at 0.05 level, then the change from Baseline (Visit 2) is transformed using normal scores and analyzed using a two-way ANCOVA model with treatment group and study center as factors and similarly transformed Baseline (Visit 2) total score as the covariate.

An a priori ordered multiple testing procedure that uses the 5% level of significance to perform each of the three comparisons is used to ensure strong control of family-wise error rate at 5% level. Specifically, the test procedure is a three stage test as follows: Stage 1: The test between escitalopram/bupropion combination and placebo is performed. If this comparison is significant at 5% level, then declare that the combination is significantly different from placebo and go to stage 2, else stop the procedure. Stage 2: The test between escitalopram/bupropion combination and bupropion is performed. If this comparison is significant at the 5% level, then declare the combination is significantly different from bupropion and go to stage 3, else stop the procedure. Stage 3: The test between escitalopram/bupropion combination and escitalopram is performed. If this comparison is significant at the 5% level, then declare the combination is significantly different from escitalopram and the study a success, else stop the procedure.

In addition, the secondary comparisons between bupropion monotherapy and placebo, as well as escitalopram monotherapy and placebo, are performed using the same ANCOVA model on change from Baseline (Visit 2) to Week 8 in MADRS total score at the 5% level of significance.

The secondary efficacy parameter is a change from Baseline (Visit 2) to Week 8 in HAMD total score. The analyses are carried out using a similar statistical model as used for the primary efficacy parameter. Pairwise comparisons between the four treatment groups (escitalopram/bupropion combination, escitalopram, bupropion and placebo) are performed at the 5% level of significance.

The additional efficacy parameters are

Change from Baseline (Visit 2) to Week 8 in MADRS total score

Change from Baseline (Visit 2) to Week 8 in HAMD total score

Change from Baseline (Visit 2) to Week 8 in CGI-S total score

CGI-I score at Week 8

Change from Baseline (Visit 2) to Week 8 in HAMA total score

Change from Baseline (Visit 2) to Week 8 in QOL score M

MADRS response rate (50% reduction from Baseline) at Week 8

MADRS remission rate (MADRS≦12) at Week 8

HAMD response rate (50% reduction from Baseline) at Week 8

HAMD remission rate (HAMD-17≦7) at Week 8

CGI-I response rate (CGI-I≦2) at Week 8

Change from Baseline (Visit 2) to Week 8 in HAMD psychomotor retardation subscale Change from Baseline (Visit 2) to Week 8 in HAMD cognitive disturbance subscale Change from Baseline (Visit 2) to Week 8 in HAMD sleep disturbance subscale Change from Baseline (Visit 2) to Week 8 in HAMD melancholia subscale Change from Baseline (Visit 2) to Week 8 in HAMD depressed mood item For continuous variables the analysis is carried out using a similar statistical model as used for the primary efficacy parameter, except for the CGI-I where the baseline score of the CGI-S are used as a covariate. For categorical variables, the analyses are carried out using a logistic regression model with treatment group and the respective baseline value as explanatory variables.

Pairwise comparisons between four treatment groups (escitalopram/bupropion combination, escitalopram, bupropion, and placebo) are performed at the 5% level of significance. Additionally, analyses for all efficacy parameters are carried out at each visit.

Results

Efficacy results based on assessments made in terms of mean change from baseline to endpoint (LOCF) are provided in Table 21 and in FIGS. 1-3.

TABLE 21

Efficacy Results: LS mean change from baseline to endpoint (LOCF)

| | MADRS 1° parameter, validated | $HAMD_{24}$ 2° parameter, validated | $HAMD_{17}$ | HAMD psycho- motor | HAMD cognit disturb | QOL | HAMA | CGI-S | CGI-I |
|---|---|---|---|---|---|---|---|---|---|
| combo vs placebo | −2.71* | −2.15* | −1.49 | −0.38 | −0.37 | 3.40* | −2.01* | −0.40* | −0.36* |
| combo vs bupro | −1.64 | −1.05 | −0.73 | −0.05 | −0.16 | 1.44 | −0.70 | −0.13 | −0.25 |
| combo vs escital | −0.20 | −1.0 | −0.74 | −0.21 | −0.08 | 1.15 | −0.09 | −0.07 | −0.03 |
| bupro vs pbo | −1.08 | −1.10 | −0.75 | −0.33 | −0.21 | 1.97 | −1.31 | −0.27 | −0.11 |
| escital vs pbo | −2.51* | −1.15 | −0.75 | −0.16 | −0.29 | 2.25 | −1.91* | −0.32* | 0.33* |

Efficacy results based on response rates are provided in Table 22. 56.5% and 46.6% of patients in the escitalopram and bupropion groups, respectively, exhibited a CGI-I response of 1 or 2, whereas 57.1% of patients in the combination group showed the same level of response. 47.3% and 43.6% of patients in the escitalopram and bupropion groups, respectively, showed an improvement of greater than or equal to 50% as measured by MADRS, whereas 47.9% of patients in the combination group showed the same level of response. Regarding response as measured by $HAMD_{24}$, 46.6% and 42.9% of patients in the escitalopram and bupropion groups, respectively, showed an improvement of greater than or equal to 50%, whereas 46.4% of patients in the combination group showed the same level of response. 35.9%, 37.6%, 39.3% of patients in the escitalopram, bupropion, and combination treatment groups, respectively, exhibited a MADRS remission of less than or equal to 12. 29.8%, 29.3%, and 28.6% of patients in the escitalopram, bupropion, and combination treatment groups, respectively, exhibited a $HAMD_{17}$ remission of less than or equal to 7.

TABLE 22

Efficacy results: Response Rates (%)

|  | CGI % response | MADRS % remission | MADRS % response | HAMD17 % remission | HAMD24 % response |
|---|---|---|---|---|---|
| combination vs. pbo | 57.14* | 39.29 | 47.86* | 28.57 | 46.43* |
| bupropion vs. pbo | 46.62 | 37.59 | 43.61 | 29.32 | 42.86 |
| escitalopram vs. pbo | 56.49* | 35.88 | 47.33* | 29.77 | 46.56* |
| placebo | 39.23 | 27.69 | 33.85 | 20.77 | 33.08 |

CGI-I response = 1 or 2
MADRS remission <=12
MADRS response >=50% improvement
HAMD17 remission <=7
HAMD24 response >=50% improvement Safety and tolerability results are provided in Table 23. Regarding early discontinuations, 21.1%, 21.6%, 18.3%, 17.1% of patients taking the placebo, bupropion, escitalopram, or a combination of bupropion and escitalopram, respectively, discontinued treatment early. 65.4%, 75.4%, 65.6%, and 76.4% of patients in the placebo, bupropion, escitalopram, or combination of bupropion and escitalopram groups, respectively, exhibited at least one Treatment Emergent Adverse Event (TEAE). The numbers and percentages of patients in the placebo, bupropion, escitalopram, or combination of bupropion and escitalopram groups exhibiting selected TEAEs are also provided in Table 23. Finally, ASEX changes separated by treatment group and sex are provided in Table 24.

TABLE 23

Safety and Tolerability Results

|  | Pbo | Bupro | Esc | Combo |
|---|---|---|---|---|
| Early Discontinuation | | | | |
| All Reasons | 28 (21.1%) | 29 (21.6%) | 24 (18.3%) | 24 (17.1%) |
| Insufficient Response | 5 (3.8%) | 4 (3.0%) | 0 | 1 (0.7%) |
| AEs | 4 (3.0%) | 10 (7.5%) | 5 (3.8%) | 6 (4.3%) |
| Incidence of TEAEs | | | | |
| Pts with at least 1 TEAE | 87 (65.4%) | 101 (75.4%) | 86 (65.6%) | 107 (76.4%) |
| Selected TEAEs | | | | |
| dry mouth | 7 (5.3%) | 13 (9.7%) | 11 (8.4%) | 26 (18.6%) |
| nausea | 8 (6.0%) | 5 (3.7%) | 10 (7.6%) | 15 (10.7%) |
| vomiting | 5 (3.8%) | 0 | 2 (1.5%) | 0 |
| constipation | 1 (0.8%) | 6 (4.5%) | 3 (2.3%) | 4 (2.9%) |
| diarrhea | 8 (6.0%) | 5 (3.7%) | 6 (4.6%) | 2 (1.4%) |
| weight decreased | 0 | 4 (3.0%) | 0 | 3 (3.1%) |
| decreased appetite | 1 (0.8%) | 5 (3.7%) | 2 (1.5%) | 7 (5.0%) |
| anorexia | 0 | 0 | 1 (0.8%) | 1 (0.7%) |
| weight increased | 0 | 0 | 3 (2.3%) | 0 |
| increased appetite | 3 (2.3%) | 3 (2.2%) | 1 (0.8%) | 0 |
| dizziness | 4 (3.0%) | 2 (1.5%) | 3 (2.3%) | 4 (2.9%) |
| somnolence | 3 (2.3%) | 2 (1.5%) | 4 (3.1%) | 4 (2.9%) |
| hypersomnia | 1 (0.8%) | 0 | 0 | 1 (0.7%) |
| sedation | 0 | 1 (0.7%) | 1 (0.8%) | 0 |
| lethargy | 0 | 2 (1.5%) | 0 | 0 |
| insomnia | 2 (1.5%) | 14 (10.4%) | 5 (3.8%) | 13 (9.3%) |
| initial insomnia | 0 | 1 (0.7%) | 0 | 2 (1.4%) |
| middle insomnia | 0 | 3 (2.2%) | 0 | 1 (0.7%) |
| early morn awakening | 0 | 2 (1.5%) | 1 (0.8%) | 1 (0.7%) |
| sleep disorder | 1 (0.8%) | 2 (1.5%) | 0 | 1 (0.7%) |
| intentional self-injury | 1 (0.8%) | 0 | 0 | 0 |
| suicidal ideation | 1 (0.8%) | 1 (0.7%) | 0 | 0 |
| completed suicide* | 1 (0.8%) | 0 | 0 | 0 |
| *a 2nd completed suicide occurred during single-blind placebo lead-in | | | | |
| libido decreased | 2 (1.5%) | 1 (0.7%) | 3 (2.3%) | 5 (3.6%) |
| libido increased | 1 (0.8%) | 0 | 0 | 0 |
| erectile dysfunction | 1 (1.8%) | 0 | 0 | 2 (3.2%) |
| orgasm abnormal | 0 | 0 | 0 | 1 (1.3%) |
| ejaculation delayed | 0 | 0 | 2 (3.9%) | 2 (3.2%) |

TABLE 24

| | ASEX Change in total scores (improvement = reduction in score) | |
|---|---|---|
| Males | placebo | −0.4773 |
| | bupropion | −1.4222 |
| | escitalopram | +0.1667 |
| | combination | −0.3333 |
| Females | placebo | −0.4762 |
| | bupropion | −1.6571 |
| | escitalopram | −1.0000 |
| | combination | −1.2836 |

In view of the foregoing results, it is surprising and unexpected that a combination of escitalopram and bupropion can be used to effectively treat central nervous system disorders.

Patents, patent applications, publications, product descriptions, and protocols are cited throughout this application, the disclosures of which are incorporated herein by reference in their entireties for all purposes.

What is claimed is:

1. A method of treating a disorder selected from the group consisting of major depressive disorder, general anxiety disorder, social anxiety disorder, panic disorder, post traumatic stress disorder, acute stress disorder, phobia, dysthymia and premenstrual dysphoric disorder in a patient in need thereof comprising daily administration of an effective amount of (a) escitalopram or a pharmaceutically acceptable salt thereof in an amount up to about 4 mg and (b) bupropion or a pharmaceutically acceptable salt thereof in an amount up to about 150 mg, wherein the treatment results in a synergistic effect.

2. The method of claim 1, wherein about 4 mg of escitalopram or a pharmaceutically acceptable salt thereof and about 150 mg of bupropion or a pharmaceutically acceptable salt are administered daily.

3. The method of claim 1, wherein the escitalopram is administered as escitalopram oxalate.

4. The method of claim 1, wherein the bupropion is administered as bupropion hydrochloride.

5. The method of claim 1, wherein the escitalopram or pharmaceutically acceptable salt thereof and the bupropion or pharmaceutically acceptable salt thereof are co-administered.

6. The method of claim 1, wherein the escitalopram or pharmaceutically acceptable salt thereof and the bupropion or pharmaceutically acceptable salt thereof are administered together in a unitary dosage form.

7. The method of claim 1, wherein the disorder is general anxiety disorder.

8. The method of claim 1, wherein the disorder is major depressive disorder.

9. The method of claim 1, wherein the disorder is social anxiety disorder.

* * * * *